(12) United States Patent
Yamamoto et al.

(10) Patent No.: US 9,316,583 B2
(45) Date of Patent: Apr. 19, 2016

(54) SPECIMEN ANALYZING METHOD AND SPECIMEN ANALYZING APPARATUS

(71) Applicant: SYSMEX CORPORATION, Kobe-shi, Hyogo (JP)

(72) Inventors: Norimasa Yamamoto, Kobe (JP); Takashi Yamato, Kobe (JP); Naohiko Matsuo, Kobe (JP); Satoshi Iguchi, Kobe (JP)

(73) Assignee: SYSMEX CORPORATION, Kobe-shi, Hyogo (JP)

( * ) Notice: Subject to any disclaimer, the term of this patent is extended or adjusted under 35 U.S.C. 154(b) by 0 days.

(21) Appl. No.: 14/677,170

(22) Filed: Apr. 2, 2015

(65) Prior Publication Data

US 2015/0211995 A1 Jul. 30, 2015

Related U.S. Application Data

(63) Continuation of application No. 14/015,358, filed on Aug. 30, 2013, now Pat. No. 9,028,756, which is a (Continued)

(30) Foreign Application Priority Data

Mar. 29, 2005 (JP) ................................ 2005-093692

(51) Int. Cl.
*G01N 21/00* (2006.01)
*G01N 21/59* (2006.01)
(Continued)

(52) U.S. Cl.
CPC ............ *G01N 21/59* (2013.01); *G01N 21/0332* (2013.01); *G01N 21/17* (2013.01);
(Continued)

(58) Field of Classification Search
CPC ................ B01L 2300/0832; B01L 2300/0627; B01L 2300/168; G01N 35/04; G01N 2035/0465; G01N 21/03; G01N 33/0031; G01N 2021/0325; G01N 35/02; G01N 35/025; G01N 21/59; G01N 2201/062; G01N 35/10; G01N 2035/00465; G01N 21/0332; G01N 21/13; G01N 21/17; G01N 2201/0231; G01N 35/00603; Y10S 436/815; Y10S 436/817; Y10S 436/11; Y10S 436/113332; Y10S 436/146666; Y10S 436/112499
USPC ........... 422/50, 400, 401, 402, 403, 404, 405, 422/408, 62, 63, 64, 65, 67, 68.1, 73, 75, 422/82.05, 82.06, 82.07, 82.08, 82.09, 98, 422/500, 501, 504, 509, 510, 511, 512, 514, 422/515, 521, 526, 547, 549, 550, 554, 556, 422/557, 558, 559, 560, 561, 562, 565, 566, 422/939, 940; 436/43, 46, 47, 164, 165, 436/169, 170, 815, 817; 435/13, 283.1, 435/287.1, 287.7, 287.8, 287.9, 288.7; 73/863.01, 864.21
See application file for complete search history.

(56) References Cited

U.S. PATENT DOCUMENTS 3,609,042 A 9/1971 Yasuda et al.
4,208,353 A 6/1980 Webster et al.
(Continued)

FOREIGN PATENT DOCUMENTS

CN 1493252 A 5/2004
EP 0 355 738 B1 2/1990
(Continued)

OTHER PUBLICATIONS

European Search Report dated Nov. 28, 2013 for corresponding European Patent Application No. 06729780.4.

*Primary Examiner* — Dennis M White
(74) *Attorney, Agent, or Firm* — Sughrue Mion, PLLC

(57) ABSTRACT

A specimen analyzing method and a specimen analyzing apparatus capable of measuring interference substances before analyzing a specimen. The method comprises a step for sucking the specimen stored in a specimen container (150) and sampling it in a first container (153), a step for optically measuring the specimen in the first container, a step for sampling the specimen in a second container (154) and preparing a specimen for measurement by mixing the specimen with a reagent in the second container, and a step for analyzing the specimen for measurement according to the results of the optical measurement of the specimen.

20 Claims, 23 Drawing Sheets

Related U.S. Application Data continuation of application No. 11/905,328, filed on Sep. 28, 2007, now Pat. No. 8,545,760, which is a continuation of application No. PCT/JP2006/305813, filed on Mar. 23, 2006.

(51) Int. Cl.
*G01N 35/02* (2006.01)
*G01N 21/17* (2006.01)
*G01N 21/03* (2006.01)
*G01N 21/31* (2006.01)
*G01N 35/00* (2006.01)

(52) U.S. Cl.
CPC ............ *G01N 21/31* (2013.01); *G01N 35/025* (2013.01); *G01N 35/00603* (2013.01); *G01N 2035/00465* (2013.01); *G01N 2201/0231* (2013.01); *G01N 2201/062* (2013.01); *Y10S 436/815* (2013.01); *Y10S 436/817* (2013.01); *Y10T 436/11* (2015.01); *Y10T 436/112499* (2015.01); *Y10T 436/113332* (2015.01); *Y10T 436/146666* (2015.01)

(56) References Cited

U.S. PATENT DOCUMENTS

| | | | |
|---|---|---|---|
| 4,313,735 A | 2/1982 | Yamashita et al. |
| 4,451,433 A | 5/1984 | Yamashita et al. |
| 4,528,159 A | 7/1985 | Liston |
| 4,668,617 A | 5/1987 | Furuta et al. |
| 4,684,252 A | 8/1987 | Makiguchi et al. |
| 4,685,801 A | 8/1987 | Minekane |
| 4,731,225 A | 3/1988 | Wakatake |
| 4,774,055 A | 9/1988 | Wakatake et al. |
| 4,778,763 A | 10/1988 | Makiguchi et al. |
| 4,896,963 A | 1/1990 | Kato |
| 5,100,622 A | 3/1992 | Mimura et al. |
| 5,337,139 A | 8/1994 | Shirasawa |
| 5,482,861 A | 1/1996 | Clark et al. |
| 5,587,129 A | 12/1996 | Kurosaki et al. |
| 5,646,046 A | 7/1997 | Fischer et al. |
| 5,698,450 A | 12/1997 | Ringrose et al. |
| 5,734,468 A | 3/1998 | McNeal |
| 6,195,158 B1 | 2/2001 | Cadell et al. |
| 6,353,471 B1 | 3/2002 | Samsoondar et al. |
| 6,388,750 B1 | 5/2002 | Liu et al. |
| 6,409,968 B1 | 6/2002 | Takahashi |
| 6,605,213 B1 | 8/2003 | Ammann et al. |
| 6,709,634 B1 | 3/2004 | Okada et al. |
| 6,797,518 B1 | 9/2004 | Jacobs et al. |
| 8,326,388 B2 | 12/2012 | Kanayama et al. |
| 2003/0026773 A1 | 2/2003 | Swaile et al. |
| 2005/0259261 A1 | 11/2005 | Harada et al. |
| 2007/0222973 A1 | 9/2007 | Hoshiko et al. |
| 2008/0070318 A1 | 3/2008 | Yamamoto et al. |

FOREIGN PATENT DOCUMENTS

| | | |
|---|---|---|
| JP | 61-82272 | 5/1986 |
| JP | 62-34095 B2 | 7/1987 |
| JP | 01-287466 | 11/1989 |
| JP | 2-223859 A | 9/1990 |
| JP | 04-130248 | 5/1992 |
| JP | 06-265554 A | 9/1994 |
| JP | 6-347466 A | 12/1994 |
| JP | 7-58263 B2 | 6/1995 |
| JP | 7-280814 A | 10/1995 |
| JP | 8-94636 A | 4/1996 |
| JP | 8-114600 A | 5/1996 |
| JP | 10-170444 A | 6/1998 |
| JP | 10-274656 A | 10/1998 |
| JP | 2001-027643 | 1/2001 |
| JP | 3229498 B2 | 9/2001 |
| WO | 98/21564 A | 5/1998 |

FIG.12

| SPECIMEN NUMBER | MEASURE-MENT ITEM | SECONDARY DISPEN-SATION FLAG | INTERFERENCE SUBSTANCE FLAG | | | WAVE-LENGTH CHANGE FLAG | HIGH-GAIN FLAG |
| --- | --- | --- | --- | --- | --- | --- | --- |
| | | | BILIRUBIN | HEMOGLOBIN | CHYLE | | |
| 000101 | PT | 0 | 0 | 0 | 0 | 0 | 0 |
| 000101 | AT III | 0 | 0 | 0 | 0 | 0 | 0 |
| 000102 | APTT | 0 | 0 | 0 | 0 | 0 | 0 |
| 000102 | FDP | 0 | 0 | 0 | 0 | 0 | 0 |
| ⋮ | ⋮ | ⋮ | ⋮ | ⋮ | ⋮ | ⋮ | ⋮ |

FLOW OF PROCESSING OF ANALYZING OPTICAL INFORMATION RECEIVED FROM FIRST OPTICAL INFORMATION ACQUISITION PORTION

SPECIMEN ANALYZING METHOD AND SPECIMEN ANALYZING APPARATUS

This is a continuation of application Ser. No. 14/015,358 filed Aug. 30, 2013, now U.S. Pat. No. 9,028,756, which is a continuation of application Ser. No. 11/905,328 filed Sep. 28, 2007, now U.S. Pat. No. 8,545,760, which is a continuation of International Application No. PCT/JP2006/305813 filed Mar. 23, 2006, which claims priority to Japanese patent application 2005-093692, filed Mar. 29, 2005, the contents of all of which are incorporated herein by reference in their entirety.

BACKGROUND OF THE INVENTION

1. Field of the Invention

The present invention relates to a specimen analyzing method and a specimen analyzing apparatus analyzing a specimen such as plasma, serum or urine.

CROSS-REFERENCE TO RELATED APPLICATIONS

The priority application number JP2005-093692, Specimen Analyzing Method and Specimen Analyzing Apparatus, Mar. 29, 2005, Norimasa Yamamoto, Takashi Yamato, Naohiko Matsuo and Satoshi Iguchi, upon which this patent application is based is hereby incorporated by reference. This application is a continuation of PCT/JP2006/305813, Specimen Analyzing Method and Specimen Analyzing Apparatus, Mar. 23, 2006, Norimasa Yamamoto, Takashi Yamato, Naohiko Matsuo and Satoshi Iguchi.

2. Description of the Background Art

In general, a specimen analyzing apparatus optically measuring and analyzing the quantity and the degree of activity of a specific substance contained in a specimen such as plasma, serum or urine is known in the field of clinical tests. Such a specimen analyzing apparatus prepares an analytical sample by adding a reagent to the specimen, and thereafter applies a light of a prescribed wavelength to the analytical sample. A specimen analyzing method obtaining analysis results by analyzing scattered light or transmitted light from the analytical sample is generally employed.

In a specimen with symptoms of hemolysis, chyle or icterus, it may be difficult to perform correct optical measurement. This is for the following reasons: When plasma is employed as the specimen, a hemolytic specimen is reddish due to a large quantity of hemoglobin contained in the specimen, although normal plasma is pale yellow and substantially transparent. And, a chylous specimen is milky due to a large quantity of lipid contained in the specimen. And, an icteric specimen is yellow or yellow-green due to a large quantity of bilirubin contained in the specimen. Thus, when a substance (interference substance) such as hemoglobin, lipid or bilirubin hindering the optical measurement is present in the specimen, a light of a specific wavelength is absorbed or an amount of a change in scattered light is insufficiently obtained, whereby it is difficult to perform correct optical measurement. Particularly in a case of a specimen with remarkable symptoms of hemolysis, chyle and icterus, it is more difficult to perform correct optical measurement, whereby there has been such inconvenience that it is difficult to obtain analysis results. Consequently, there has been such inconvenience that analytical efficiency of the specimen analyzing apparatus may be reduced.

In order to solve the aforementioned inconvenience, therefore, there is generally proposed a specimen test automation system automatically determining the state of a specimen before analyzing the specimen with the specimen analyzing apparatus. Such a specimen test automation system is disclosed in Japanese Patent Laying-Open No. 7-280814, for example. The specimen test automation system disclosed in Japanese Patent Laying-Open No. 7-280814 has a dispenser dispensing a specimen from a specimen container and an automatic analyzing apparatus analyzing the specimen dispensed by the dispenser, and further measures presence/absence of hemolysis, chyle and icterus (interference substances) in the specimen with a separately provided "hemolysis, chyle and icterus measuring apparatus" before analysis of a serum specimen with the automatic analyzing apparatus and collates the results of the measurement with requested test items for the automatic analyzing apparatus. The system so controls the automatic analyzing apparatus as to analyze only requested test items whose analysis results are not influenced by the interference substances contained in the specimen and not to analyze requested test items whose analysis results are influenced by the interference substances contained in the specimen, on the basis of the results of the collation. When it is determined to perform analysis with the specimen analyzing apparatus, a specimen in a blood collection tube is dispensed into a sample cup for the automatic analyzing apparatus by the dispenser, and the sample cup is transported to the automatic analyzing apparatus. And a reagent is added into the specimen dispensed into the sample cup, thereby analysis of the requested test items whose analysis results are not influenced by the interference substances is performed. When there are no requested test items analyzable in relation to the serum specimen are present as the result of collation, the dispenser is so controlled as not to dispense the serum specimen. Thus, the specimen test automation system according to the aforementioned Japanese Patent Laying-Open No. 7-280814 suppresses reduction of the analytical efficiency of the automatic analyzing apparatus.

The aforementioned Japanese Patent Laying-Open No. 7-280814 discloses a structure spectrally measuring the states of hemolysis, chyle and icterus from outside the blood collection tube. However, a bar code label for specifying the specimen is generally stuck on the blood collection tube, and this bar code label may be such a hindrance that it is not possible to correctly measure the interference substances.

On the other hand, U.S. Pat. No. 6,797,518 discloses a structure measuring interference substances with respect to a specimen remaining on the forward end of a measuring chip sucking the specimen, while U.S. Pat. No. 5,734,468 discloses a structure sucking a specimen with a probe having a needle and a transparent portion and measuring interference substances with the transparent portion of this probe.

SUMMARY OF THE INVENTION

The present invention has been proposed in order to solve the aforementioned problem, and aims at providing a novel specimen analyzing method and a novel specimen analyzing apparatus capable of measuring interference substances before analyzing a specimen.

In order to attain the aforementioned object, a specimen analyzing method according to a first aspect of the present invention comprises steps of sucking a specimen stored in a specimen container and sampling the specimen into a first container, optically measuring the specimen in the first container, sampling the specimen into a second container and preparing a measurement sample by mixing the specimen with a reagent in the second container, and analyzing the measurement sample according to a result of the optical measurement of the specimen.

A specimen analyzing apparatus according to a second aspect of the present invention comprises a first sampling portion for sucking a specimen stored in a specimen container and sampling the specimen into a first container, an optical measurement portion for optically measuring the specimen sampled into the first container, a second sampling portion for sampling the specimen into a second container, a sample preparation portion for preparing a measurement sample by mixing the specimen with a reagent in the second container, an analysis portion for analyzing the measurement sample in the second container, and a control portion for controlling an analyzing operation by the analysis portion according to a result of the optical measurement of the specimen.

BRIEF DESCRIPTION OF THE DRAWINGS

FIG. 12 is a diagram showing a specimen analysis table output to a display portion of the control unit of the specimen analyzing apparatus according to the first embodiment shown in FIG. 1.

DESCRIPTION OF THE PREFERRED EMBODIMENTS

Embodiments of the present invention are now described with reference to the drawings.

First Embodiment

First, the overall structure of a specimen analyzing apparatus 1 according to a first embodiment of the present invention is described with reference to FIGS. 1 to 10.

The specimen analyzing apparatus 1 according to the first embodiment of the present invention is an apparatus for optically measuring and analyzing the quantity and the degree of activity of a specific substance related to coagulative and fibrinolytic functions of blood, and employs plasma as a specimen. The specimen analyzing apparatus 1 according to the first embodiment optically measures the specimen with a coagulation time method, a synthetic substrate method and immunonephelometry. The coagulation time method is a measuring method detecting the process of coagulation of the specimen as a change of transmitted light or scattered light. The synthetic substrate method is a measuring method detecting a change of absorbance in the process of color development of a color-producing synthetic substrate added to the specimen on the basis of a change of transmitted light. The immunonephelometry is a measuring method detecting a change of absorbance resulting from antigen-antibody reaction of an antibody sensitizing reagent such as a latex reagent added to the specimen on the basis of a change of transmitted light. The specimen analyzing apparatus 1 is constituted of a detection mechanism portion 2, a transport mechanism portion 3 arranged on the front side of the detection mechanism portion 2 and a control unit 4 electrically connected to the detection mechanism portion 2, as shown in FIG. 1.

Figure 2:
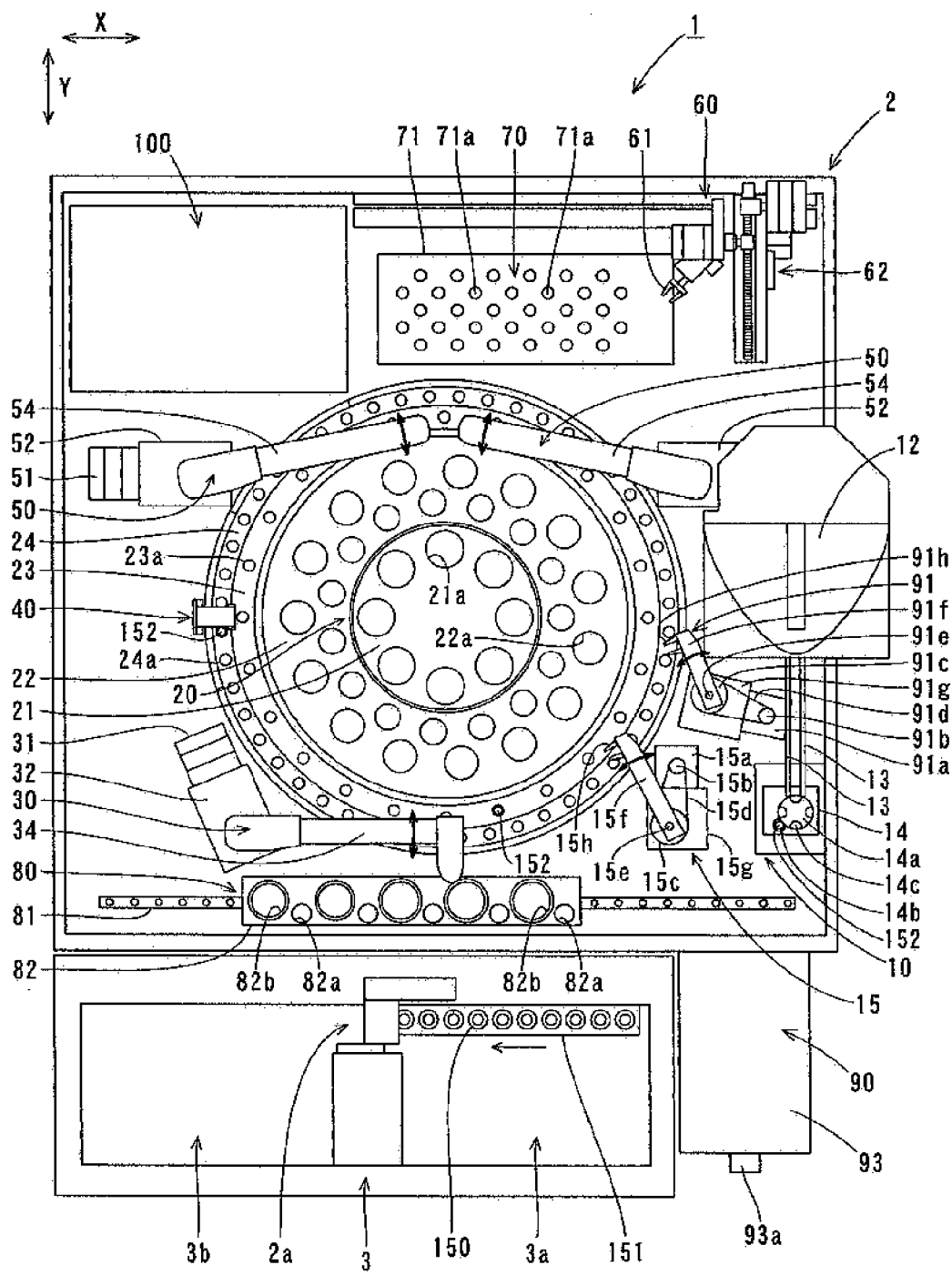
FIG. 2 is a plan view showing a detection mechanism portion and a transport mechanism portion of the specimen analyzing apparatus according to the first embodiment shown in FIG. 1.
Figure 4:
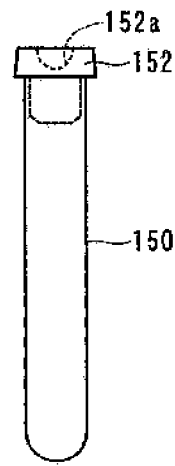
FIG. 4 is a front elevational view of a specimen container of the specimen analyzing apparatus according to the first embodiment shown in FIG. 1.

The transport mechanism portion 3 is so formed as to automatically supply specimens to the detection mechanism portion 2 by transporting a rack 151 receiving a plurality of (according to the first embodiment, 10) test tubes 150 storing the specimens to a position corresponding to a suctional position 2a (see FIG. 2) of the detection mechanism portion 2. Each test tube 150 is provided with an opening on the upper portion thereof, and a lid 152 is fitted into the opening, as shown in FIG. 4. A recess portion 152a stuck with a nozzle 35 described later is formed in this lid 152. This transport mechanism portion 3 has a rack set region 3a for setting the rack 151 receiving the test tubes 150 storing untreated specimens and a rack storage region 3b for storing the rack 151 receiving the test tubes 150 storing treated specimens. In other words, the rack 151 set on the rack set region 3a is transported to the position corresponding to the suctional position 2a of the detection mechanism portion 2, as shown in FIG. 2. After the detection mechanism portion 2 performs dispensation (primary dispensation) of the specimens stored in the test tubes 150, the rack 151 is transported to and stored in the rack storage region 3b. A plurality of racks 150 can be set on the rack set region 3a of the transport mechanism portion 3.

Figure 1:
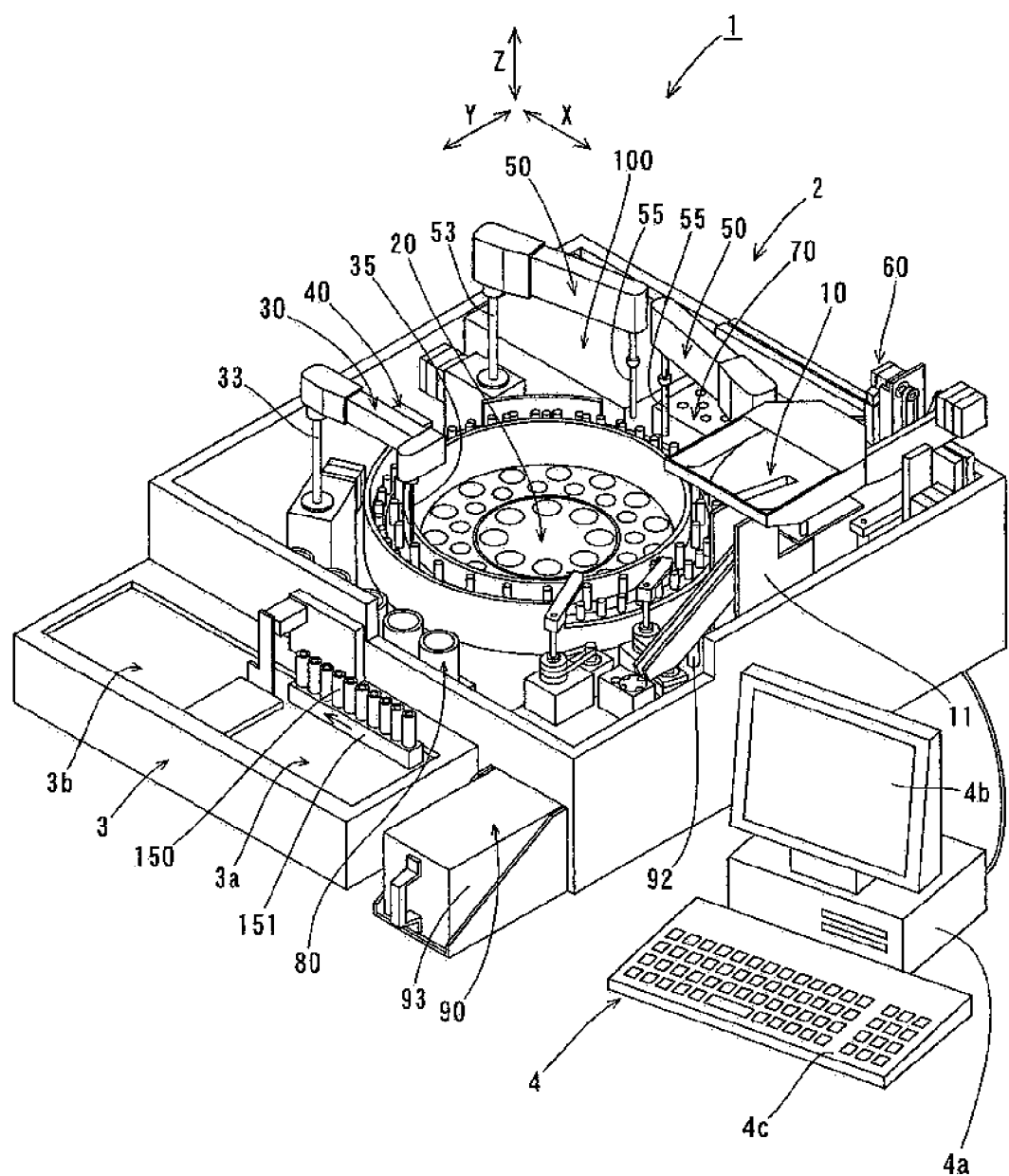
FIG. 1 is a perspective view showing the overall structure of a specimen analyzing apparatus according to a first embodiment of the present invention.

The control unit 4 is formed by a personal computer (PC) or the like, and includes a control portion 4a, a display portion 4b and a keyboard 4c, as shown in FIG. 1. The control portion 4a controls operations of the detection mechanism portion 2 and the transport mechanism portion 3, and has a function for analyzing optical information of the specimens obtained in the detection mechanism portion 2. This control portion 4a is formed by a CPU, a ROM, a RAM and the like. The display portion 4b is provided for displaying information related to interference substances (hemoglobin, chyle (lipid) and bilirubin) present in the specimens and analysis results obtained in the control portion 4a.

Figure 3:
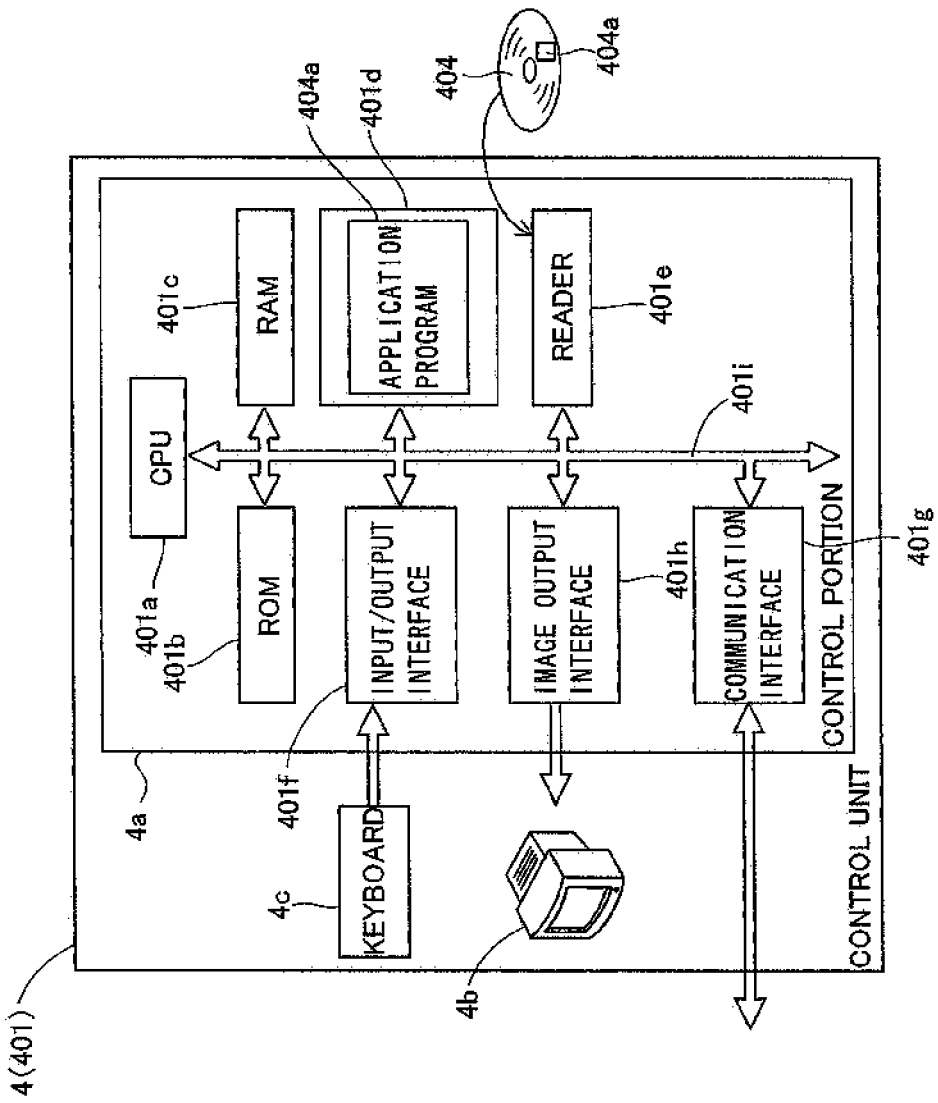
FIG. 3 is a block diagram showing the structure of a control unit shown in FIG. 1.

The structure of the control unit 4 is now described. The control unit 4 is constituted of a computer 401 mainly constituted of the control portion 4a, the display portion 4b and the keyboard 4c, as shown in FIG. 3. The control portion 4a is mainly constituted of a CPU 401a, a ROM 401b, a RAM 401c, a hard disk 401d, a reader 401e, an input/output interface 401f, a communication interface 401g and an image output interface 401h, and the CPU 401a, the ROM 401b, the RAM 401c, the hard disk 401d, the reader 401e, the input/output interface 401f, the communication interface 401g and the image output interface 401h are connected with each other by a bus 401i.

The CPU 401a can run computer programs stored in the ROM 401b and computer programs loaded in the RAM 401c. This CPU 401a runs an application program 404a described later, so that the computer 401 functions as the control unit 4.

The ROM 401b is constituted of a mask ROM, a PROM, an EPROM, an EEPROM or the like, and the computer programs run by the CPU 401a and data employed therefor are recorded therein.

The RAM 401c is constituted of an SRAM or a DRAM. The RAM 401c is employed for reading the computer programs recorded in the ROM 401b and the hard disk 401d. Further, the RAM 401c is utilized as a working area of the CPU 401a when running these computer programs.

An operating system and various computer programs such as application programs to be run by the CPU 401a as well as data employed for running the computer programs are installed in the hard disk 401d. The application program 404a for blood coagulation analysis processing is also installed in this hard disk 401d.

The reader 401e is constituted of a flexible disk drive, a CD-ROM drive or a DVD-ROM drive, and can read computer programs or data recorded in a portable recording medium 404. The potable recording medium 404 stores the application program 404a for blood coagulation analysis processing, while the computer 401 can read the application program 404a related to the present invention from the portable recording medium 404 and install this application program 404a in the hard disk 401d.

The aforementioned application program 404a is not only provided by the portable recording medium 404, but can also be provided from an external apparatus communicably connected with the computer 401 by an electric communication line (whether wire or wireless) through the said electric communication line. For example, it is also possible that the said application program 404a is stored in a hard disk of a server computer on the Internet, so that the computer 401 accesses this server computer, downloads the application program 404a and installs the same in the hard disk 401d.

Further, the operating system such as Windows (registered trademark) manufactured and sold by Microsoft, U.S.A., for example, providing graphical user interface environment is installed in the hard disk 401d. In the following description, it is assumed that the application program 404a according to this embodiment operates on this operating system.

The output interface 401f is constituted of a serial interface such as USB, IEEE 1394 or RS-232C, a parallel interface such as SCSI, IDE or IEEE 1284, an analog interface formed by a D/A converter, an A/D converter etc. or the like, for example. The keyboard 4c is connected to the input/output interface 401f, so that the user can input data into the computer 401 by using this keyboard 4c.

The communication interface 401g is Ethernet (registered trademark) interface, for example. The computer 401 can transmit/receive data to/from the detection mechanism 2 by this communication interface 401g with a prescribed communication protocol.

The image output interface 401h is connected to the display portion 4b constituted of an LCD or a CRT, for outputting an image signal corresponding to image data supplied from the CPU 401a to the display portion 4b. The display portion 4b displays an image (screen) according to the input image signal.

The detection mechanism portion 2 is enabled to acquire optical information related to the specimens by optically measuring the specimens supplied from the transport mechanism portion 3. The specimen analyzing apparatus 1 according to the first embodiment optically measures the specimens dispensed from the test tubes 150 of the transport mechanism portion 3 into cuvettes 153 and 154 (see FIG. 2) of the detection mechanism portion 2. The cuvettes 153 are held in holding portions 24a of a primary dispensation table 24 described later, while the cuvettes 154 are held in holding portions 23a of a secondary dispensation table 23 described later. The detection mechanism portion 2 includes a cuvette supply portion 10, a rotational transport portion 20, a specimen dispensation arm 30, a first optical information acquisition portion 40, two reagent dispensation arms 50, a cuvette transfer portion 60, a second optical information acquisition portion 70, an emergency specimen set portion 80, a cuvette disposal portion 90 and a fluid portion 100, as shown in FIGS. 1 and 2.

The cuvette supply portion 10 is enabled to successively supply the plurality of cuvettes 153 and 154 to the rotational transport portion 20. This cuvette supply portion 10 includes a hopper 12 mounted on the apparatus body through a bracket 11 (see FIG. 1), two induction plates 13 provided under the hopper 12, a fulcrum 14 arranged on the lower ends of the two induction plates 13 and a supply catcher portion 15 provided at a prescribed interval from the fulcrum 14, as shown in FIG. 2. The two induction plates 13 are arranged parallelly to each other at an interval smaller than the diameter of flange portions 153a and 154a (see FIG. 6) of the cuvettes 153 and 154 and larger than the diameter of body portions 153b and 154b (see FIG. 6) of the cuvettes 153 and 154. The cuvettes 153 and 154 supplied into the hopper 12 are so formed as to slide down and move toward the fulcrum 14, with the flange portions 153a and 154a engaging with the upper surfaces of the two induction plates 13.

The fulcrum 14 has a rotating portion 14a rotatably provided with respect to the fulcrum 14 and a recess portion 14b formed adjacently to the rotating portion 14a, as shown in FIG. 2. Four notches 14c are formed on the outer periphery of the rotating portion 14a every prescribed angle (90°). These four notches 14c are provided for receiving the cuvettes 153 and 154 induced by the two induction plates 13 one by one. The recess portion 14b is enabled to receive the cuvettes 153 and 154 from the notches 14c of the rotating portion 14a, and provided as a supply start position for supplying the cuvettes 153 and 154 to the rotational transport portion 20 with the supply catcher portion 15.

The supply catcher portion 15 is provided for supplying the cuvettes 153 and 154 from the cuvette supply portion 10 to the rotational transport portion 20. This supply catcher portion 15 has a drive motor 15a, a pulley 15b connected to the drive motor 15a, another pulley 15c provided at a prescribed interval from the pulley 15b, a drive transmission belt 15d attached to the pulleys 15b and 15c, an arm portion 15f mounted on the pulley 15c through a shaft 15e and a driving portion 15g for vertically moving the arm portion 15f. The drive motor 15a functions as a drive source for rotating the arm portion 15f about the shaft 15e between the fulcrum 14 and the rotational transport portion 20. A chuck portion 15h for holding and grasping each of the cuvettes 153 and 154 is provided on the forward end of the arm portion 15f.

The rotational transport portion 20 is provided for transporting the cuvettes 153 and 154 supplied from the cuvette supply portion 10 and reagent containers (not shown) storing reagents added to the specimens stored in the cuvettes 153 and 154 in a rotational direction. This rotational transport portion 20 is constituted of a circular reagent table 21, an annular reagent table 22 arranged on the outer side of the circular reagent table 21, an annular secondary dispensation table 23 arranged on the outer side of the annular reagent table 22 and an annular primary dispensation table 24 arranged on the outer side of the annular secondary dispensation table 23. The primary dispensation table 24, the secondary dispensation table 23, the reagent table 21 and the reagent table 22 are rotatable in both of the clockwise direction and the counterclockwise direction respectively, and the respective tables are enabled to rotate independently of each other.

Figure 6:
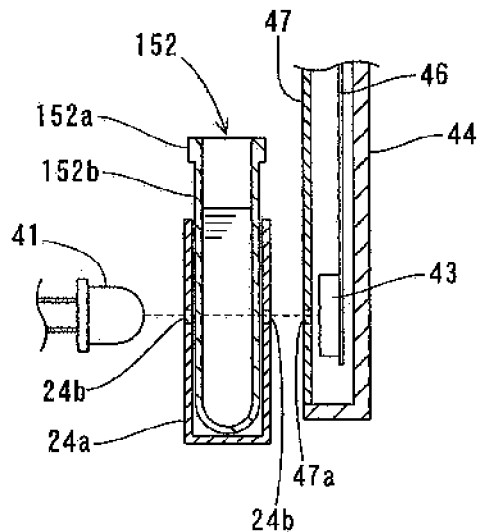
FIG. 6 is a sectional view schematically showing the first optical information acquisition portion according to the first embodiment shown in FIG. 5.

The reagent tables 21 and 22 include a plurality of holes 21a and 22a provided at prescribed intervals respectively. The holes 21a and 22a of the reagent tables 21 and 22 are provided for receiving a plurality of reagent containers (not shown) storing various reagents added when measurement samples are prepared from the specimens. Further, the primary dispensation table 24 and the secondary dispensation table 23 include a plurality of cylindrical holding portions 24a and 23a provided at prescribed intervals respectively. The holding portions 24a and 23a are provided for holding the cuvettes 153 and 154 supplied from the cuvette supply portion 10 respectively. The specimens are dispensed from the test tubes 150 of the transport mechanism portion 3 into the cuvettes 153 held in the holding portions 24a of the primary dispensation table 24 in primary dispensation processing. Then, the specimens are dispensed from the cuvettes 153 held on the primary dispensation table 24 into the cuvettes 154 held in the holding portions 23a of the secondary dispensation table 23 in secondary dispensation processing. Each holding portion 24a is provided with a pair of small holes 24b on opposite positions of side portions of the holding portion 24a, as shown in FIG. 6. The pair of small holes 24b are provided for passing lights emitted from a light-emitting diode (LED) 41, described later, of the first optical information acquisition portion 40 therethrough.

The specimen dispensation arm 30 shown in FIG. 2 has a function for dispensing the specimens stored in the test tubes 150 transported by the transport mechanism portion 3 to the suctional position 2a of the detection mechanism portion 2 into the cuvettes 153 held in the holding portions 24a of the primary dispensation table 24 of the rotational transport portion 20. The specimen dispensation arm 30 also has a function for dispensing the specimens from the cuvettes 153 held in the holding portions 24a of the primary dispensation table 24 of the rotational transport portion 20 into the cuvettes 154 held in the holding portions 23a of the secondary dispensation table 23. This specimen dispensation arm 30 includes a drive motor 31, a drive transmission portion 32 connected to the drive motor 31 and an arm portion 34 mounted on the drive transmission portion 32 through a shaft 33 (see FIG. 1). The drive transmission portion 32 is enabled to rotate the arm portion 34 about the shaft 33 and to vertically move the same with driving force from the driving motor 31. The nozzle 35 (see FIG. 1) is mounted on the forward end of the arm portion 34. This nozzle 35 has a function of sucking the specimens by piercing into the recess portions 152a (see FIG. 4) of the lids 152 fitted into the openings of the test tubes 150.

Figure 5:
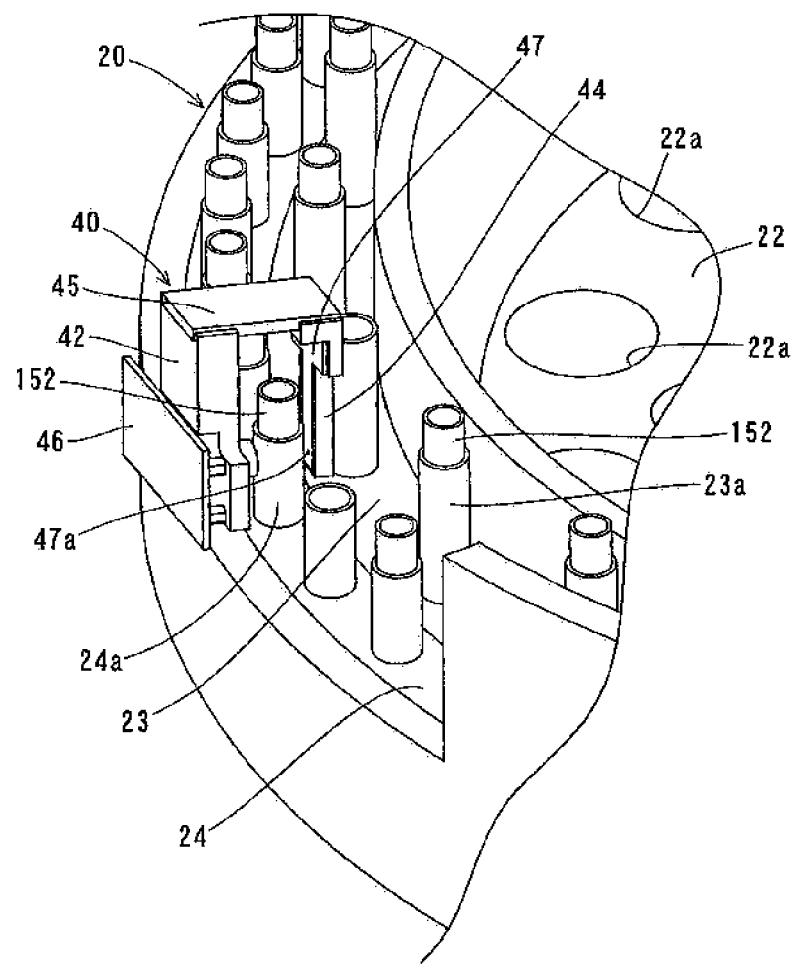
FIG. 5 is a perspective view showing a first optical information acquisition portion of the specimen analyzing apparatus according to the first embodiment shown in FIG. 1.

The first optical information acquisition portion 40 is so formed as to acquire optical information from the specimens, in order to detect presence/absence of interference substances in the specimens before addition of the reagents and types and degrees of inclusion thereof. This first optical information acquisition portion 40 acquires optical information from the specimens to which the reagents have been added, in advance of optical measurement of the specimens with the second optical information acquisition portion 40. The first optical information acquisition portion 40 is arranged above the primary dispensation table 24 of the rotational transport portion 20 as shown in FIGS. 2 and 5, and acquires optical information from the specimens stored in the cuvettes 153 held in the holding portions 24a of the primary dispensation table 24. The first optical information acquisition portion 40 includes the light-emitting diode (LED) 41 (see FIG. 6) serving as a light source, a light-emission-side holder 42, a photoelectric conversion element 43 (see FIG. 6), a light-receiving-side holder 44, a bracket 45 and a substrate 46, as shown in FIG. 5.

The light-emitting diode 41 is provided to be capable of applying lights to the cuvette 153 held in each holding portion 24a of the primary dispensation table 24, as shown in FIG. 6. This light-emitting diode 41 is so controlled by a controller 46d (see FIG. 7) of the substrate 46 as to be capable of periodically successively emitting lights of three different wavelengths. The light-emitting diode 41 according to the first embodiment can emit a blue light having a wavelength of 430 nm, a green light having a wavelength of 565 nm and a red light having a wavelength of 627 nm. The light-emission-side holder 42 is provided for supporting the light-emitting diode 41 (see FIG. 6) and the substrate 46, as shown in FIG. 5. The photoelectric conversion element 43 has a function for detecting the lights emitted from the light-emitting diode 41 and passed through the cuvettes 153 and converting the same to electric signals. The light-receiving-side holder 44 is mounted on the light-emission-side holder 42 through the bracket 45 as shown in FIG. 5, and formed in a shape capable of storing the photoelectric conversion element 43 (see FIG. 6) therein. A lid member 47 provided with a slit 47a on a prescribed position is mounted on this light-receiving-side holder 44. The lights emitted from the light-emitting diode 41 and transmitted through the cuvettes 153 held in the holding portions 24a of the primary dispensation table 24 are detected by the photoelectric conversion element 43 through the slit 47a of the lid member 47.

Figure 7:
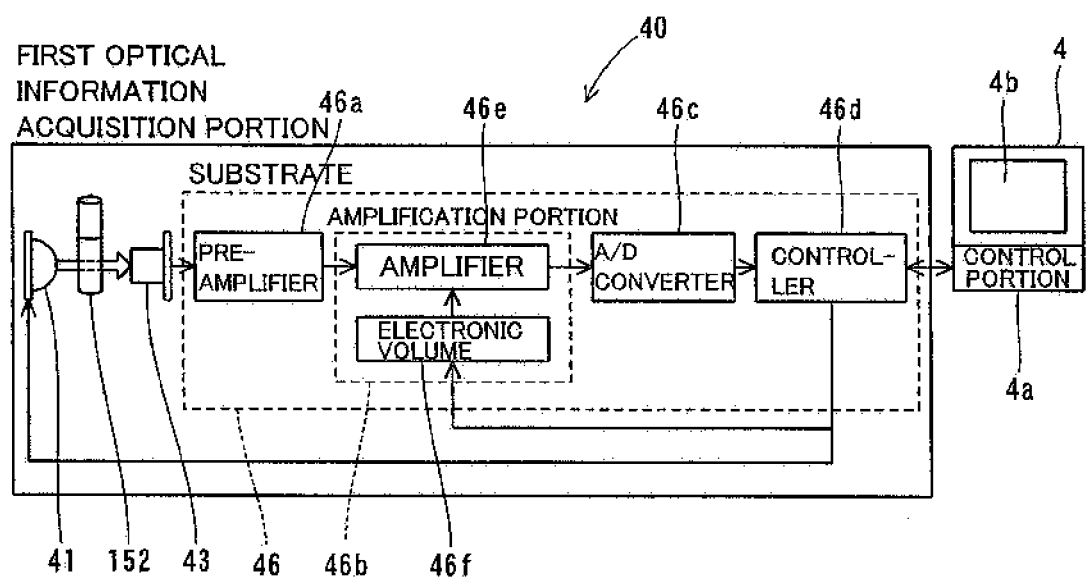
FIG. 7 is a block diagram showing the structure of the first optical information acquisition portion according to the first embodiment shown in FIG. 5.

The substrate 46 has a function of amplifying the electric signals received from the photoelectric conversion element 43 and transmitting the same to the control portion 4a of the control unit 4. The substrate 46 is constituted of a preamplifier 46a, an amplification portion 46b, an A/D converter 46c and the controller 46d, as shown in FIG. 7. The amplification portion 46b has an amplifier 46e and an electronic volume 46f. The preamplifier 46a and the amplifier 46e are provided for amplifying the electric signals received from the photoelectric conversion element 43. The amplifier 46e of the amplification portion 46b is enabled to control the gain (amplification factor) of the amplifier 46e by inputting a control signal received from the controller 46d into the electronic volume 46f. The A/D converter 46c is provided for converting the electric signals (analog signals) amplified by the amplifier 46e to digital signals.

The controller 46d is so formed as to change the gain (amplification factor) of the amplifier 46e coincidentally with periodic changes of the wavelengths (430 nm, 565 nm and 627 nm) of the lights emitted from the light-emitting diode 41. Further, the controller 46d is electrically connected to the control portion 4a of the control unit 4 as shown in FIG. 7, and transmits data of the digital signals acquired in the first optical information acquisition portion 40 to the control portion 4a of the control unit 4. Thus, the control unit 4 analyzes the data of the digital signals received from the first optical information acquisition portion 40, thereby obtaining absorbances of the specimens stored in the cuvettes 153 with respect to the three lights emitted from the light-emitting diode 41, and analyzing presence/absence of interference substances in the specimens and types and degrees of inclusion thereof. The control unit 4 determines whether or not to measure the specimens with the second optical information acquisition portion 70 and controls a method of analyzing detection results received from the second optical information acquisition portion 70 and a method of displaying the analysis results on the basis of the analysis results.

The two reagent dispensation arms 50 shown in FIG. 2 are provided for dispensing the reagents stored in the reagent containers (not shown) placed in the holes 21a and 22a of the reagent tables 21 and 22 into the cuvettes 154 of the secondary dispensation table 23. These two reagent dispensation arms 50 add the reagents to the specimens stored in the cuvettes 154 of the secondary dispensation table 23 so that the measurement samples are prepared. The two reagent dispensation arms 50 include drive motors 51, drive transmission portions 52 connected to the drive motors 51 and arm portions 54 mounted on the drive transmission portions 52 through shafts 53 (see FIG. 1) respectively, as shown in FIG. 2. The drive transmission portions 52 are enabled to rotate the arm portions 54 about the shafts 53 and to vertically move the same with driving force from the drive motors 51. Nozzles 55 (see FIG. 1) for sucking and discharging the reagents are mounted on the forward ends of the arm portions 54.

The cuvette transfer portion 60 is provided for transferring the cuvettes 154 storing the measurement samples between the secondary dispensation table 23 of the rotational transport portion 20 and a cuvette receiving portion 71 of the second optical information acquisition portion 70. The cuvette transfer portion 60 includes a chuck portion 61 for holding and grasping each cuvette 154 and a driving mechanism portion 62 for moving the chuck portion 61 in directions X, Y and Z (see FIG. 1) respectively, as shown in FIG. 2. The driving mechanism portion 62 has a function for vibrating the chuck portion 61. Thus, the measurement sample stored in each cuvette 154 can be easily stirred by vibrating the chuck portion 61 in the state grasping the cuvette 154.

The second optical information acquisition portion 70 has a function for heating the measurement samples prepared by adding the reagents to the specimens and optically measuring the measurement samples. This second optical information acquisition portion 70 is constituted of the cuvette receiving portion 71 and a detection portion 72 (see FIG. 8) arranged under the cuvette receiving portion 71, as shown in FIG. 2. The cuvette receiving portion 71 is provided with a plurality of insertion holes 71a for inserting the cuvettes 154. Further, the cuvette receiving portion 71 stores a heating mechanism (not shown) for heating the cuvettes 154 inserted into the insertion holes 71a to a prescribed temperature.

Figure 8:
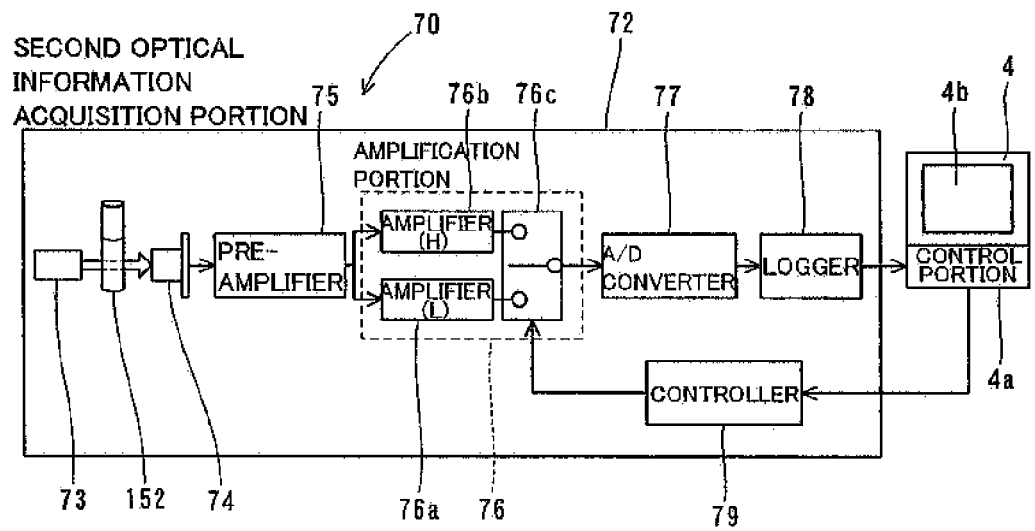
FIG. 8 is a block diagram showing the structure of a second optical information acquisition portion of the specimen analyzing apparatus according to the first embodiment shown in FIG. 1.
Figure 9:
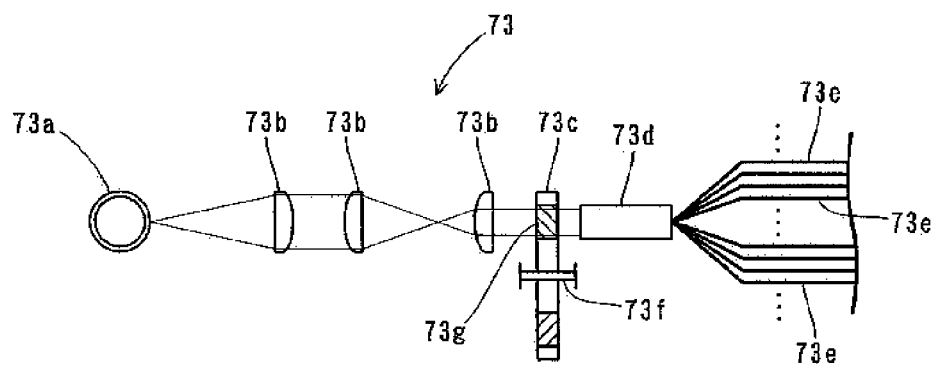
FIG. 9 is a schematic diagram showing the structure of a lamp portion of the second optical information acquisition portion according to the first embodiment shown in FIG. 8.

According to the first embodiment, the detection portion 72 of the second optical information acquisition portion 70 is enabled to optically measure the measurement samples stored in the cuvettes 154 inserted into the insertion holes 71a under a plurality of conditions. This detection portion 72 includes a lamp portion 73 serving as a light source, a photoelectric conversion element 74, a preamplifier 75, an amplification portion 76, an A/D converter 77, a logger 78 and a controller 79, as shown in FIG. 8. The lamp portion 73 has a halogen lamp 73a, three condenser lenses 73b, a discoidal filter member 73c, an optical fiber 73d and branched optical fibers 73e, as shown in FIG. 9. The three condenser lenses 73d are provided for condensing a light emitted from the halogen lamp 73a on the filter member 73c.

Figure 10:
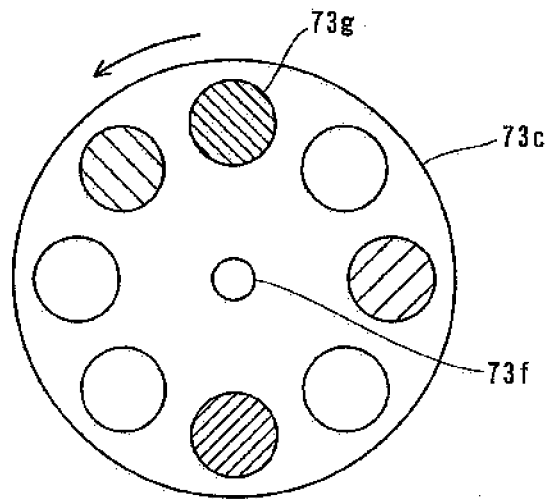
FIG. 10 is a plan view showing a filter member of the lamp portion according to the first embodiment shown in FIG. 9.

According to the first embodiment, the filter member 73c is rendered rotatable about a shaft 73f, as shown in FIGS. 9 and 10. This filter member 73c is provided with a plurality of filters 73g having different transmission wavelengths at prescribed angular intervals (at intervals of 45° according to the first embodiment) along the rotational direction of the filter member 73c, as shown in FIG. 10. As hereinabove described, the filter member 73c including the plurality of filters 73g having different transmission wavelengths is rendered rotatable so that the light emitted from the halogen lamp 73a can be successively passed through the plurality of filters 73g having different transmission wavelengths, whereby a plurality of lights having different wavelengths can be successively supplied to the optical fiber 73d. According to the first embodiment, the filter member 73c can supply lights having five different wavelengths of 340 nm, 405 nm, 575 nm, 660 nm and 800 nm to the optical fiber 73d. The lights having the wavelengths of 340 nm and 405 nm are employed for measurement by the synthetic substrate method respectively. The lights having the wavelengths of 575 nm and 800 nm are employed for measurement by immunonephelometry respectively. The light having the wavelength of 660 nm is employed for measurement by the coagulation time method. The branched optical fibers 73e are provided for branching the lights received from the optical fiber 73d thereby supplying the lights to the cuvettes 154 inserted into the plurality of insertion holes 71a of the cuvette receiving portion 71 respectively.

The photoelectric conversion element 74 shown in FIG. 8 has a function for detecting the lights received from the lamp portion 73 and transmitted through the measurement samples stored in the cuvettes 154 inserted into the insertion holes 71a of the cuvette receiving portion 71 and converting the same to electric signals. The preamplifier 75 is provided for amplifying the electric signals received from the photoelectric conversion element 74.

According to the first embodiment, the amplification portion 76 includes an amplifier (L) 76a having a prescribed gain (amplification factor), an amplifier (H) 76b having a higher gain (amplification factor) than the amplifier (L) 76a and a changeover switch 76c, as shown in FIG. 8. According to the first embodiment, the electric signals received from the preamplifier 75 are input in both of the amplifier (L) 76a and the amplifier (H) 76b. The amplifier (L) 76a and the amplifier (H) 76b are provided for further amplifying the electric signals received from the preamplifier 75. The changeover switch 76c is provided for selecting whether to output the electric signals received from the amplifier (L) 76a to the A/D converter 77 or to output the electric signals received from the amplifier (H) 76b to the A/D converter 77. This changeover switch 76c is so formed as to perform a switching operation by receiving a control signal from the controller 79.

The A/D converter 77 is provided for converting the electric signals (analog signals) received from the amplifier 76 to digital signals. The logger 78 has a function for temporarily preserving the data of the digital signals received from the A/D converter 77. This logger 78 is electrically connected to the control portion 4a of the control unit 4, and transmits the data of the digital signals acquired in the second optical information acquisition portion 70 to the control portion 4a of the control unit 4. Thus, the control unit 4 analyzes the data of the digital signals transmitted from the second optical information acquisition portion 70 on the basis of the analysis results of the previously acquired data of the digital signals received from the first optical information acquisition portion 40, and displays the results on the display portion 4b.

The emergency specimen set portion 80 shown in FIG. 2 is provided for performing specimen analysis processing on specimens requiring emergent treatment. This emergency specimen set portion 80 is enabled to interrupt the specimen analysis processing, performed on the specimens supplied from the transport mechanism portion 3, by emergency specimens. The emergency specimen set portion 80 includes a rail 81 so provided as to extend in the direction X and an emergency specimen rack 82 movable along the rail 81. This emergency specimen rack 82 is provided with test tube insertion holes 82a for inserting test tubes (not shown) storing the emergency specimens and reagent container insertion holes 82b for inserting reagent containers (not shown) storing reagents.

The cuvette disposal portion 90 is provided for disposing the cuvettes 153 from the rotational transport portion 20. The cuvette disposal portion 90 is constituted of a disposal catcher portion 91, a disposal hole 92 (see FIG. 1) provided at a prescribed interval from the disposal catcher portion 91 and a disposal box 93 set under the disposal hole 92, as shown in FIG. 2. The disposal catcher portion 91 is provided for moving the cuvettes 153 and 154 from the rotational transport portion 20 into the disposal box 93 through the disposal hole 92 (see FIG. 1). This disposal catcher portion 91 has a drive motor 91a, a pulley 91b connected to the drive motor 91a, another pulley 91c provided at a prescribed interval from the pulley 91b, a drive transmission belt 91d attached to the pulleys 91b and 91c, an arm portion 91f mounted on the pulley 91c through a shaft 91e and a driving portion 91g for vertically moving the arm portion 91f. The drive motor 91a functions as a drive source for rotating the arm portion 91f about the shaft 91e between the rotational transport portion 20 and the disposal hole 92. A chuck portion 91h for holding and grasping each of the cuvettes 153 and 154 is provided on the forward end of the arm portion 91f. A grasp portion 93a grasped by the user for drawing out the disposal box 93 toward the front side of the apparatus is mounted on the disposal box 93.

The fluid portion 100 shown in FIG. 1 is provided for supplying a liquid such as a detergent to the nozzles 35 and 55 provided on the respective dispensation arms in shutdown processing of the specimen analyzing apparatus 1.

A specimen analyzing operation of the specimen analyzing apparatus 1 according to the first embodiment of the present invention is now described with reference to FIGS. 1, 11 and 12.

First, the power sources for the detection mechanism portion 2 and the control unit 4 of the specimen analyzing apparatus 1 shown in FIG. 1 are brought into ON states respectively, whereby the specimen analyzing apparatus 1 is initialized at a step S1. Thus, an operation for returning a mechanism for moving the cuvettes 153 and 154 and the respective dispensation arms to initial positions, initialization of the application program 404a stored in the hard disk 401d of the control unit 4 etc. are performed. At a step S2, the user inputs specimen analysis information. In other words, the user inputs information in the columns of specimen numbers and measurement items of a specimen analysis table (see FIG. 12) output to the display portion 4b of the control unit 4 with the keyboard 4c of the control unit 4. The specimen analysis information is preserved in the RAM 401c of the control portion 4a.

The specimen analysis table shown in FIG. 12 is now described. Numbers ("000101" etc.) for identifying the individual specimens are input in the column of specimen numbers. Symbols ("PT", "ATIII" etc.) indicating measuring methods adopted for the specimens are input in the column of measurement items associated with the specimen numbers. "PT" (prothrombin time) and "APTT (activated partial thromboplastin time) in the measurement items are items subjected to measurement with the coagulation time method. "ATIII" (antithrombin III) in the measurement items is an item subjected to measurement with the synthetic substrate method. "FDP" (fibrin decomposition product) in the measurement items is an item subjected to measurement with the immunonephelometry.

The specimen analysis table is provided with items of secondary dispensation flags, interference substance flags including three subitems of bilirubin, hemoglobin and chyle, wavelength change flags and high-gain flags. These items, set to OFF (displayed with "0" in the table) in the initialization at the step S1, are changed to ON (displayed with "1" in the table) in response to the analysis results of the optical information received from the first optical information acquisition portion 40. FIG. 12 shows a state where all items are OFF. A state where any secondary dispensation flag is ON indicates that the corresponding specimen is the object of secondary dispensation as to the corresponding measurement item. A state where any flag of bilirubin, hemoglobin or chyle is ON indicates an operation of outputting a message stating that there is a high possibility that the corresponding specimen is influenced by bilirubin, hemoglobin or chyle to the display portion 4b of the control unit 4 as to the corresponding measurement item. A state where all flags of bilirubin, hemoglobin and chyle are ON is such a state that influence by the interference substance is so remarkable that it is difficult to determine which one of bilirubin, hemoglobin and chyle influences the corresponding specimen, and indicates an operation of outputting a message stating that there is a high possibility that the specimen is influenced by the interference substance (the type is not specified) to the display portion 4b of the control unit 4. A state where any wavelength change flag is ON indicates that optical information acquired with the light of a wavelength (800 nm) different from the light of the normal wavelength (660 nm) is regarded as the object of analysis as to the corresponding measurement item. A state where any high-gain flag is ON indicates that optical information acquired with a gain (amplification factor) higher than the normal gain (amplification factor) of the amplifier 46e is regarded as the object of analysis.

While the reagent containers (not shown) storing the reagents necessary for preparing the measurement samples and the test tubes 150 storing the specimens are set on prescribed positions respectively, the user inputs analyzing operation starting. Thus, the analyzing operation for each specimen is started at a step S3. After terminating a prescribed specimen analyzing operation, the CPU 401a determines whether or not a shutdown instruction for the specimen analyzing apparatus 1 has been input at a step S4. If the CPU 401a determines that the shutdown instruction for the specimen analyzing apparatus 1 has not been input at the step S4, the process returns to the step S2 so that the user inputs another specimen analysis information. If the CPU 401a determines that the shutdown instruction for the specimen analyzing apparatus 1 has been input at the step S4, on the other hand, shutdown processing is performed at a step S5. Thus, cleaning of the nozzles 35 and 55 provided on the respective dispensation arms shown in FIG. 1 or the like is performed and thereafter the power sources for the detection mechanism portion 2 and the control unit 4 of the specimen analyzing apparatus 1 automatically enter OFF states, so that the specimen analyzing operation of the specimen analyzing apparatus 1 is terminated.

Figure 11:
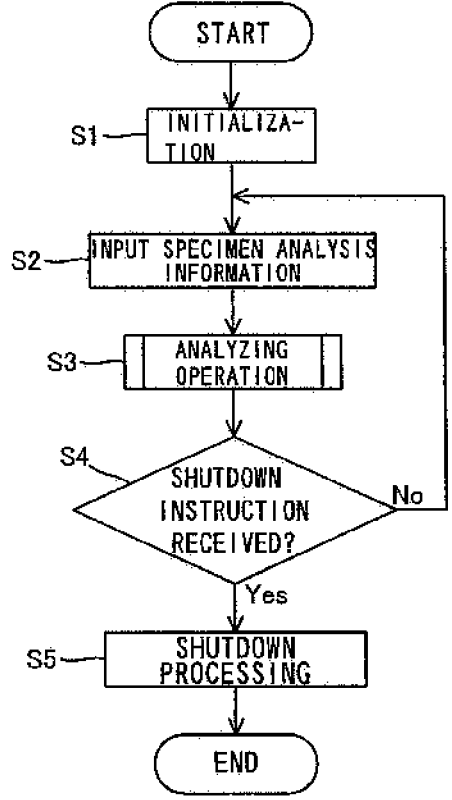
FIG. 11 is a flow chart showing a control method of the specimen analyzing apparatus according to the first embodiment shown in FIG. 1.

The specimen analyzing operation of the specimen analyzing apparatus 1 at the aforementioned step S3 of FIG. 11 is now described in detail with reference to FIGS. 1, 2 and 13. The user inputs the analyzing operation starting, so that the transport mechanism portion 3 shown in FIG. 2 transports the rack 151 receiving the test tubes 150 storing the specimens at a step S11. Thus, the rack 151 of the rack set region 3a is transported to the position corresponding to the suctional position 2a of the detection mechanism portion 2. At a step S12, the nozzle 35 (see FIG. 1) of the specimen dispensation arm 30 sucks a prescribed quantity of the specimen from each test tube 150. The drive motor 31 of the specimen dispensation arm 30 is driven for moving the nozzle 35 of the specimen dispensation arm 30 to a position above each cuvette 153 held on the primary dispensation table 24 of the rotational transport portion 20. At a step S13, the nozzle 35 of the specimen dispensation arm 30 discharges the specimen into the cuvette 153 of the primary dispensation table 24, so that primary dispensation processing is performed.

Then, the primary dispensation table 24 is rotated for transporting the cuvette 153 into which the specimen has been dispensed to a position allowing measurement with the first optical information acquisition portion 40. Thus, the first optical information acquisition portion 40 optically measures the specimen and acquires optical information from the specimen at a step S14. More specifically, the photoelectric conversion element 43 first successively detects the lights of the three different wavelengths (430 nm, 565 nm and 627 nm) emitted from the light-emitting diode (LED) 41 and transmitted through the specimen stored in the cuvette 153 held in the corresponding holding portion 24a (see FIG. 6) of the primary dispensation table 24. Then, the preamplifier 46a (see FIG. 7) and the amplifier 46e amplify electric signals converted by the photoelectric conversion element 43, while the A/D converter 46c converts the same to digital signals. Thereafter the controller 46d transmits the data of the digital signals to the control portion 4a of the control unit 4. Thus, the first optical information acquisition portion 40 completes acquisition of the optical information (data of the digital signals) with respect to the specimen. At a step S15, the CPU 401a of the control unit 4 analyzes the optical information of the specimen.

According to the first embodiment, the CPU 401a of the control unit 4 determines whether or not the specimen stored in the cuvette 153 held in the holding portion 24a of the primary dispensation table 24 is the object of secondary dispensation at a step S16, on the basis of the results of the analysis at the step S15. If determining that the specimen stored in the cuvette 153 held on the primary dispensation table 24 is not the object of secondary dispensation at the step S16, the CPU 401a outputs a message stating that the influence by the interference substance (at least one substance selected from the group consisting of bilirubin, hemoglobin and chyle (including a case where the interference substance is hard to specify)) contained in the specimen is so remarkable that it is difficult to perform reliable analysis to the display portion 4b of the control unit 4 at a step S17. If the CPU 401a determines that the specimen stored in the cuvette 153 held in the holding portion 24a of the primary dispensation table 24 is the object of secondary dispensation at the step S16, on the other hand, the nozzle 35 of the specimen dispensation arm 30 sucks a prescribed quantity of the specimen from the cuvette 153 held in the holding portion 24a of the primary dispensation table 24 at a step S18. Thereafter the nozzle 35 of the specimen dispensation arm 30 discharges the prescribed quantity of the specimen into the plurality of cuvettes 154 of the secondary dispensation table 23 respectively, so that secondary dispensation processing is performed.

The reagent dispensation arms 50 are driven for adding the reagents stored in the reagent containers placed on the reagent tables 21 and 22 to the specimens stored in the cuvettes 154 of the secondary dispensation table 23. Thus, the measurement samples are prepared at a step S19. Then, the cuvettes 154 of the secondary dispensation table 23 storing the measurement samples are moved into the insertion holes 71a of the cuvette receiving portion 71 of the second optical information acquisition portion 70 with the chuck portion 61 of the cuvette transfer portion 60.

According to the first embodiment, the detection portion 72 of the second optical information acquisition portion 70 optically measures the measurement sample stored in each cuvette 154 under a plurality of conditions at a step S20, thereby acquiring a plurality (10 types) of optical information from the measurement sample. More specifically, the heating mechanism (not shown) heats the cuvette 154 inserted into the corresponding insertion hole 71a of the cuvette receiving portion 71 to the prescribed temperature. Thereafter the lamp portion 73 of the detection portion 72 (see FIG. 8) applies lights to the cuvette 154 of the cuvette receiving portion 71. The lamp portion 73 periodically emits lights of five different wavelengths (340 nm, 405 nm, 575 nm, 660 nm and 800 nm) due to the rotation of the filter member 73c. The photoelectric conversion element 74 successively detects the aforementioned lights of the respective wavelengths emitted from the lamp portion 73 and transmitted through the cuvette 152 and the measurement sample in the cuvette 152. The electric signals corresponding to the lights of the five different wavelengths converted by the photoelectric conversion element 74 are amplified by the preamplifier 75, and thereafter successively input in the amplification portion 76.

In the amplification portion 76, the electric signals corresponding to the lights of the five different wavelengths received from the preamplifier 75 are input in the amplifier (H) 76b having the high amplification factor and the amplifier (L) 76a having the normal amplification factor respectively. The controller 79 controls the changeover switch 76c, so that the electric signals amplified by the amplifier (H) 76b are output to the A/D converter 77, and the electric signals amplified by the amplifier (L) 76a are thereafter output to the A/D converter 77. The changeover switch 76c is repetitively switched in response to the timing of the rotation of the filter member 73c in the lamp portion 73. Thus, the amplification portion 76 amplifies the electric signals corresponding to the lights of the five different wavelengths with two different amplification factors respectively, and repetitively outputs 10 types of electric signals in total to the A/D converter 77. The 10 types of electric signals are converted to digital signals by the A/D converter 77, temporarily stored in the logger 78, and thereafter successively transmitted from the controller 79 to the control portion 4a of the control unit 4. Thus, the second optical information acquisition portion 70 completes acquisition of the plurality (10 types) of optical information (data of digital signals) with respect to the measurement sample.

At a step S21, the CPU 401a of the control unit 4 analyzes optical information determined as suitable for analysis among the plurality (10 types) of optical information with respect to the measurement sample received from the second optical information acquisition portion 70, on the basis of the analysis results of the previously acquired optical information (data of digital signals) received from the first optical information acquisition portion 40. At a step S22, the CPU 401a of the control unit 4 determines whether or not the analysis results of the measurement sample obtained at the step S21 can be output. If determining that the analysis results of the measurement sample obtained at the step S21 cannot be output at the step S22, the CPU 401a outputs a message stating that the influence by the interference substance (chyle) contained in the measurement sample is so remarkable that it is difficult to perform reliable analysis to the display portion 4b of the control unit 4 at the step S17. As the case of making the aforementioned determination from the step S22 to the step S17, a case where the analysis results of the data of the electric signal corresponding to the light having the wavelength of 800 nm cannot be output in the measurement item measured with the coagulation time method or the like can be listed in the first embodiment. If determining that the analysis results of the measurement sample obtained at the step S21 can be output at the step S22, on the other hand, the CPU 401a outputs the analysis results of the measurement sample to the display portion 4b of the control unit 4 at a step S23.

Figure 13:
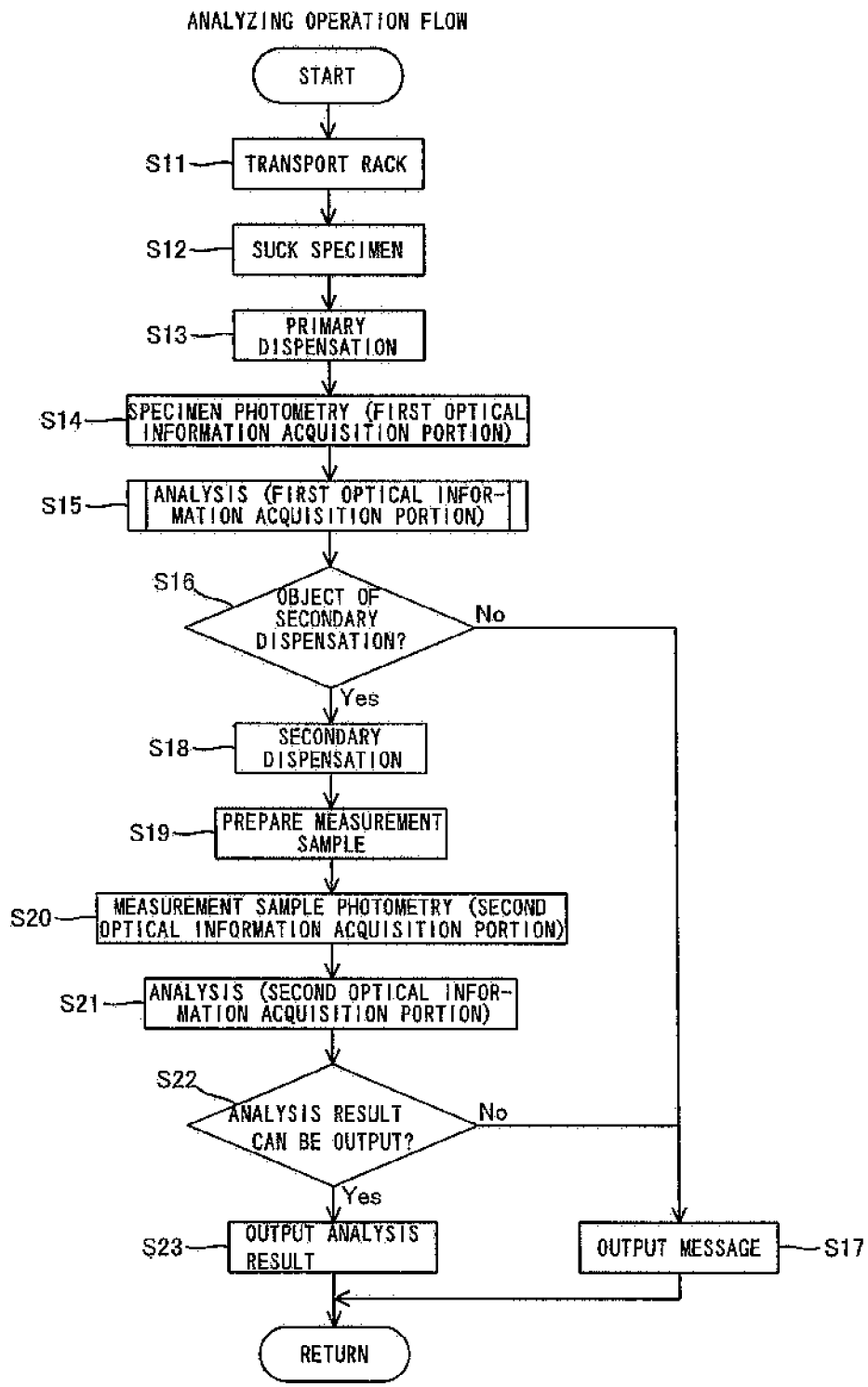
FIG. 13 is a flow chart showing the procedure of a specimen analyzing operation of the specimen analyzing apparatus according to the first embodiment shown in FIG. 1.

The method of analyzing the optical information received from the first optical information acquisition portion 40 at the step S15 shown in FIG. 13 is now described in detail with reference to FIGS. 13 to 16. The CPU 401a of the control unit 4 analyzes the optical information received from the first optical information acquisition portion 40. The optical information of the specimen acquired in the first optical information acquisition portion 40 is transmitted to the control portion 4a of the control unit 4, so that absorbances of the specimen with respect to the lights of the respective wavelengths (430 nm, 565 nm and 627 nm) are calculated at a step S31 shown in FIG. 14. The absorbance A is a value obtained with the light transmittance T (%) of the specimen according to the following equation (1):

$$A = -\log 10(T/100) \quad (1)$$

At a step S32, a determination is made as to whether or not the absorbance of the specimen with respect to the light having the wavelength of 430 nm is greater than 1.5. When it is determined that the absorbance of the specimen with respect to the light having the wavelength of 430 nm is less than 1.5 at the step S32, the item of the secondary dispensation flag indicating that the specimen is the object of secondary dispensation with the ON-state in the specimen analysis table is changed from OFF ("0" in the table) to ON ("1" in the table) at a step S33, and the process returns to the step S16 of FIG. 13. When it is determined that the absorbance of the specimen with respect to the light having the wavelength of 430 nm is greater than 1.5 at the step S32, on the other hand, a determination is made at a step S34 as to whether or not the value of "P" is greater than 10. "P" is a value obtained by "−(absorbance of specimen with respect to light having wavelength of 565 nm−absorbance of specimen with respect to light having wavelength of 430 nm)/(565−430)". When it is determined that the value of "P" is greater than 10 at the step S34, a determination is made at a step S35 of FIG. 15 as to whether or not the measurement item of the specimen is a measurement item employing the synthetic substrate method.

When it is determined that the measurement item of the specimen is not a measurement item employing the synthetic substrate method at the step S35, the item of the secondary dispensation flag indicating that the specimen is the object of secondary dispensation with the ON-state in the specimen analysis table is changed from OFF ("0" in the table) to ON ("1" in the table) at a step S36, and the process returns to the step S16 of FIG. 13. When it is determined that the measurement item of the specimen is a measurement item employing the synthetic substrate method at the step S35, on the other hand, a determination is made at a step S37 as to whether or not the value of "absorbance with respect to light having wavelength of 430 nm×dilution magnification" is at least 0.2. The dilution magnification is the dilution magnification of the specimen in a case where a measurement sample of the measurement item has been prepared from this specimen (when it is determined that this specimen is the object of secondary dispensation at the step S16, a prescribed quantity of this specimen is dispensed into the corresponding cuvette 154 of the secondary dispensation table 23 in response to the measurement item (step S18), and a prescribed type and a prescribed quantity of reagent is added thereto so that the measurement sample is prepared (step S19). Therefore, the aforementioned dilution magnification is previously decided in response to the measurement item). When it is determined that the value of "absorbance with respect to light having wavelength of 430 nm×dilution magnification" is at least 0.2 at the step S37, the flag of the item of bilirubin indicating that there is a high possibility that the specimen is influenced by bilirubin with the ON-state in the specimen analysis table is changed from OFF ("0" in the table) to ON ("1" in the table) at a step S38, and the process returns to the step S16 of FIG. 13. When it is determined that the value of "absorbance with respect to light having wavelength of 430 nm×dilution magnification" is less than 0.2 at the step S37, on the other hand, the items of the secondary dispensation flag indicating that the specimen is the object of secondary dispensation with the ON-state in the specimen analysis table, the bilirubin flag indicating that there is a high possibility that the specimen is influenced by bilirubin with the ON-state and the high-gain flag indicating that the optical information acquired with the high gain (amplification factor) is regarded as the object of analysis with the ON-state are changed from OFF ("0" in the table) to ON ("1" in the table) at steps S39, S40 and S41 respectively, and the process returns to the step S16 of FIG. 13.

Figure 14:
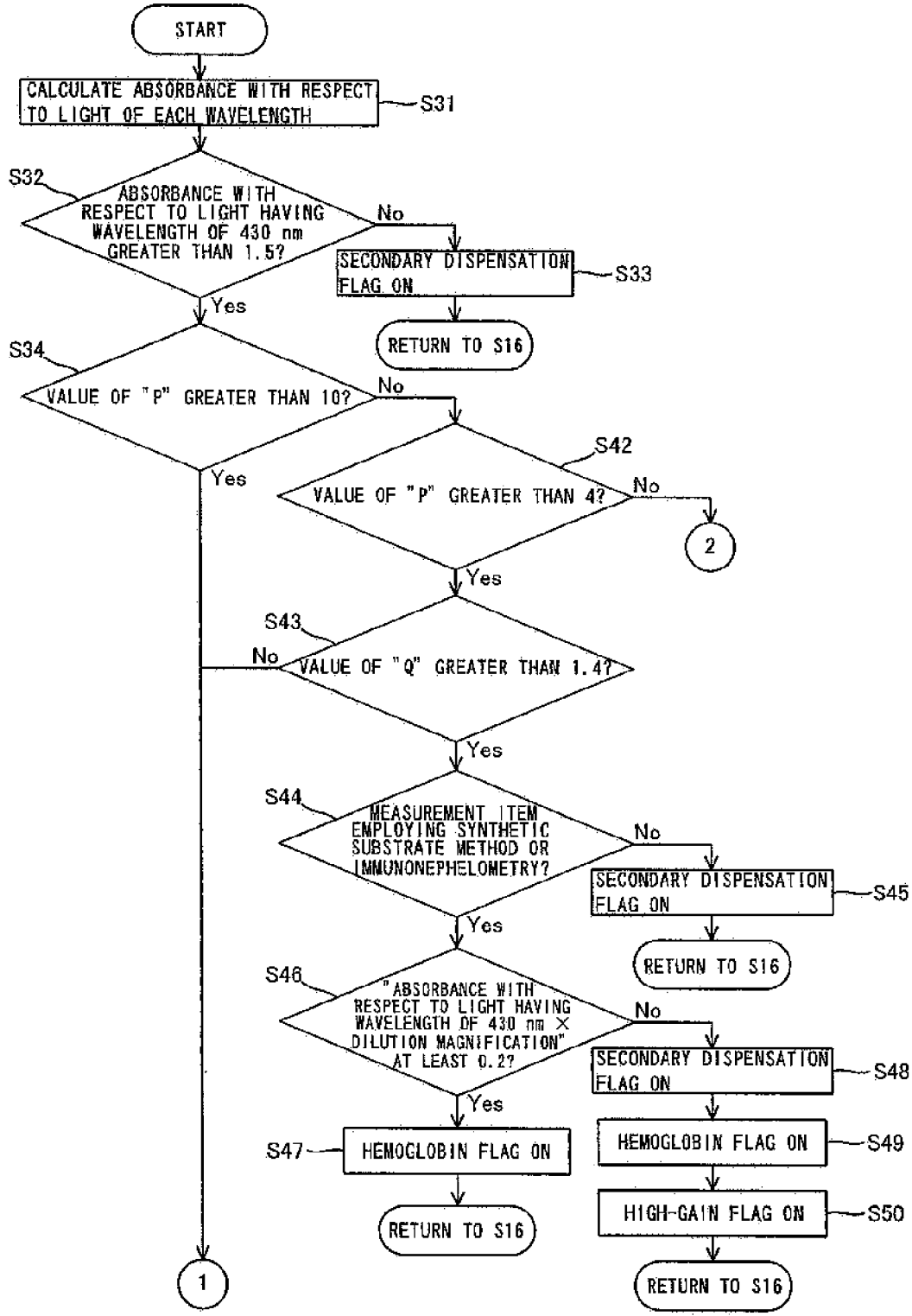
FIG. 14 is a flow chart for illustrating analysis processing for optical information from the first optical information acquisition portion according to the first embodiment shown in FIG. 5.
Figure 15:
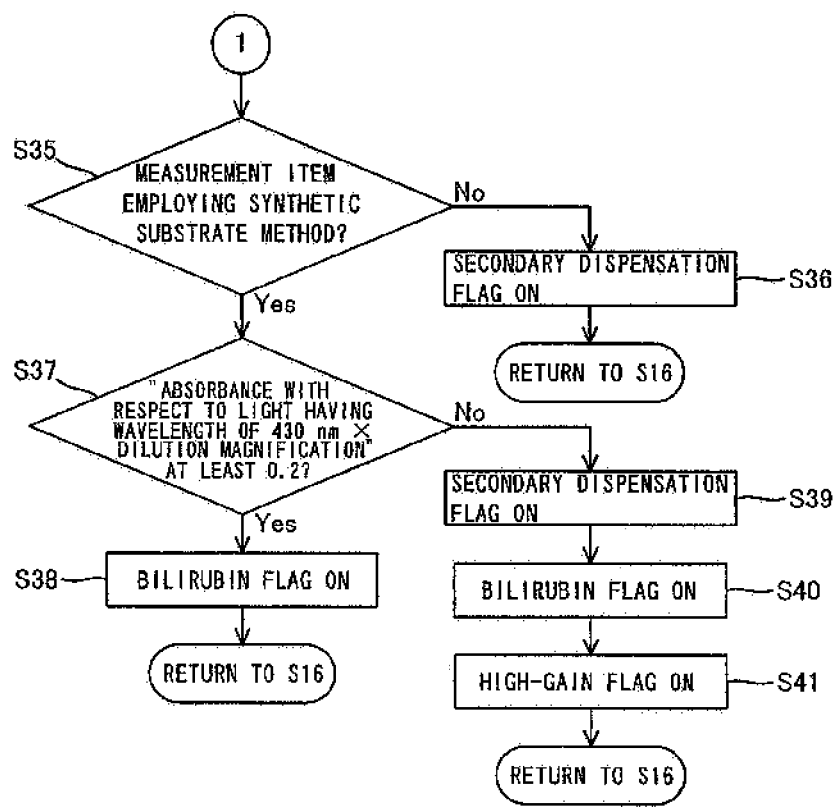
FIG. 15 is a flow chart for illustrating the analysis processing for the optical information from the first optical information acquisition portion according to the first embodiment shown in FIG. 5.

When it is determined that the value of "P" is less than 10 at the step S34 shown in FIG. 14, a determination is made at a step S42 as to whether or not the value of "P" is greater than 4. When it is determined that the value of "P" is greater than 4 at the step S42, a determination is made at a step S43 as to whether or not the value of "Q" is greater than 1.4. "Q" is a value obtained by "−(absorbance of specimen with respect to light having wavelength of 627 nm−absorbance of specimen with respect to light having wavelength of 565 nm)/(627−565)". When it is determined that the value of "Q" is not greater than 1.4 at the step S43, the process advances to the step S35 of FIG. 15, so that a determination is made as to whether or not the measurement item of the specimen is a measurement item employing the synthetic substrate method, as described above. When it is determined that the value of "Q" is greater than 1.4 at the step S43 of FIG. 14, on the other hand, a determination is made at a step S44 as to whether or not the measurement item of the specimen is a measurement item employing the synthetic substrate method or immunonephelometry.

When it is determined that the measurement item of the specimen is not a measurement item employing the synthetic substrate method or immunonephelometry at the step S44, the item of the secondary dispensation flag indicating that the specimen is the object of secondary dispensation with the ON-state in the specimen analysis table is changed from OFF ("0" in the table) to ON ("1" in the table) at a step S45, and the process returns to the step S16 of FIG. 13. When it is determined that the measurement item of the specimen is a measurement item employing the synthetic substrate method or immunonephelometry at the step S44, on the other hand, a determination is made at a step S46 as to whether or not the value of "absorbance with respect to light having wavelength of 430 nm×dilution magnification" is at least 0.2. When it is determined that the value of "absorbance with respect to light having wavelength of 430 nm×dilution magnification" is at least 0.2 at the step S46, the flag of the item of hemoglobin indicating that there is a high possibility that the specimen is influenced by hemoglobin with the ON-state in the specimen analysis table is changed from OFF ("0" in the table) to ON ("1" in the table) at a step S47, and the process returns to the step S16 of FIG. 13. When it is determined that the value of "absorbance with respect to light having wavelength of 430 nm×dilution magnification" is not at least 0.2 (less than 0.2) at the step S46, on the other hand, the items of the secondary dispensation flag indicating that the specimen is the object of secondary dispensation with the ON-state in the specimen analysis table, the hemoglobin flag indicating that there is a high possibility that the specimen is influenced by hemoglobin with the ON-state and the high-gain flag indicating that the optical information acquired with the high gain (amplification factor) is regarded as the object of analysis with the ON-state are changed from OFF ("0" in the table) to ON ("1" in the table) at steps S48, S49 and S50 respectively, and the process returns to the step S16 of FIG. 13.

Figure 16:
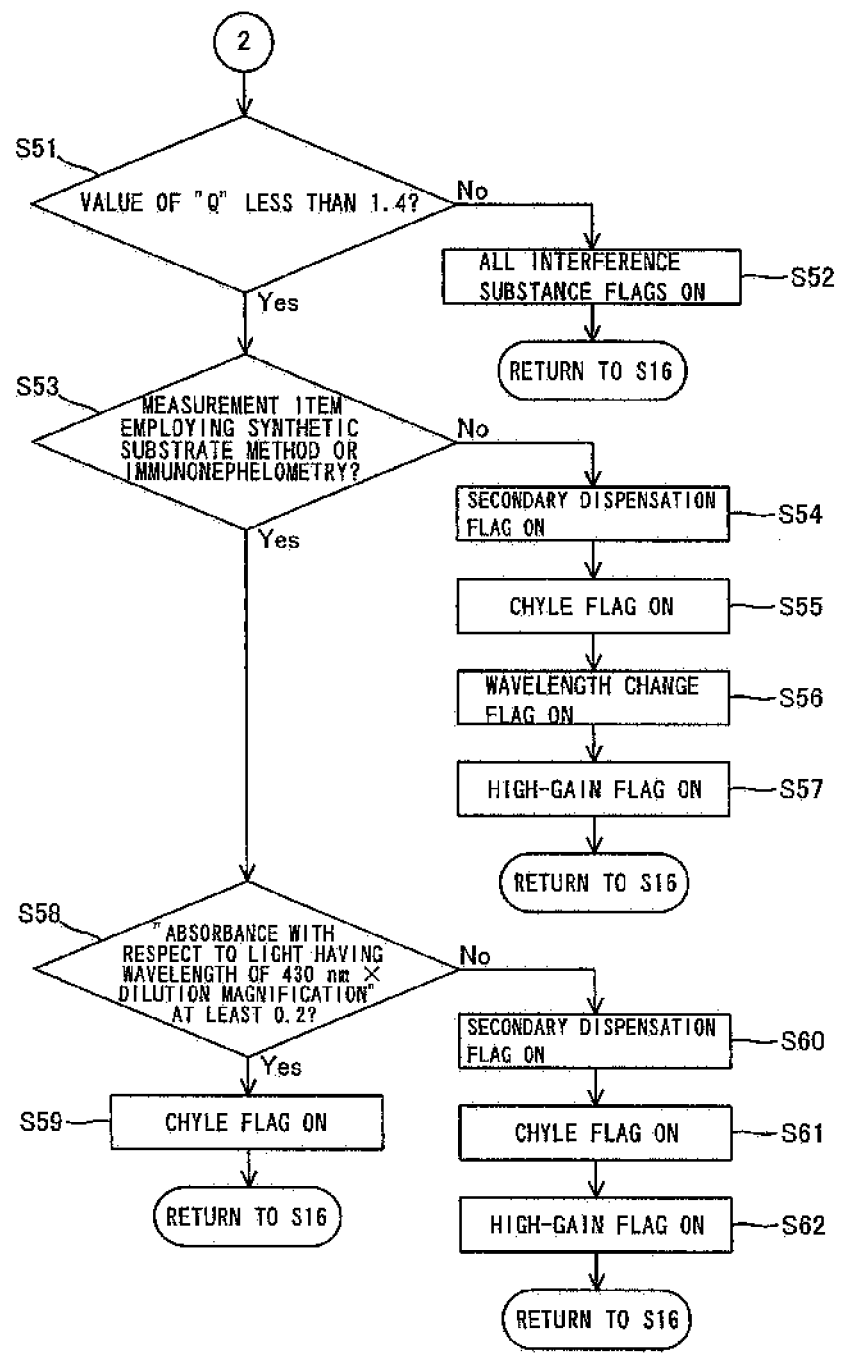
FIG. 16 is a flow chart for illustrating the analysis processing for the optical information from the first optical information acquisition portion according to the first embodiment shown in FIG. 5.

When it is determined that the value of "P" is not greater than 4 (less than 4) at the step S42, on the other hand, a determination is made at a step S51 of FIG. 16 as to whether or not the value of "Q" is less than 1.4. When it is determined that the value of "Q" is not less than 1.4 (greater than 1.4) at the step S51, all of the three flags of bilirubin, hemoglobin and chyle of the interference substance flags in the specimen analysis table are changed from OFF ("0" in the table) to ON ("1" in the table) at a step S52, and set to indicate that the influence by the interference substance is so remarkable that it is difficult to determine which one of bilirubin, hemoglobin and chyle influences the corresponding specimen. Then, the process returns to the step S16 of FIG. 13. When it is determined that the value of "Q" is less than 1.4 at the step S51, on the other hand, a determination is made at a step S53 as to whether or not the measurement item of the specimen is a measurement item employing the synthetic substrate method or immunonephelometry. When it is determined that the measurement item of the specimen is not a measurement item employing the synthetic substrate method or immunonephelometry at the step S53, the items of the secondary dispensation flag indicating that the specimen is the object of secondary dispensation with the ON-state in the specimen analysis table, the chyle flag indicating that there is a high possibility that the specimen is influenced by chyle with the ON-state, the wavelength change flag indicating that the optical information acquired with the light having the wavelength (800 nm) different from the light having the normal wavelength (660 nm) is regarded as the object of analysis with the ON-state and the high-gain flag indicating that the optical information acquired with the high gain (amplification factor) is regarded as the object of analysis with the ON-state are changed from OFF ("0" in the table) to ON ("1" in the table) at steps S54, S55, S56 and S57 respectively, and the process returns to the step S16 of FIG. 13. When it is determined that the measurement item of the specimen is a measurement item employing the synthetic substrate method or immunonephelometry at the step S53, on the other hand, a determination is made at a step S58 as to whether or not "absorbance with respect to light having wavelength of 430 nm×dilution magnification" is at least 0.2.

When it is determined that "absorbance with respect to light having wavelength of 430 nm×dilution magnification" is at least 0.2 at the step S58, the flag of the item of chyle indicating that there is a high possibility that the specimen is influenced by chyle with the ON-state in the specimen analysis table is changed from OFF ("0" in the table) to ON ("1" in the table) at a step S59, and the process returns to the step S16 of FIG. 13. When it is determined that "absorbance with respect to light having wavelength of 430 nm×dilution magnification" is not at least 0.2 (less than 0.2) at the step S58, on the other hand, the items of the secondary dispensation flag indicating that the specimen is the object of secondary dispensation with the ON-state in the specimen analysis table, the chyle flag indicating that there is a high possibility that the specimen is influenced by chyle with the ON-state and the high-gain flag indicating that the optical information acquired with the high gain (amplification factor) is regarded as the object of analysis with the ON-state are changed from OFF ("0" in the table) to ON ("1" in the table) at steps S60, S61 and S62 respectively, and the process returns to the step S16 of FIG. 13.

According to the first embodiment, as hereinabove described, the specimen dispensation arm 30 sampling the specimen stored in each test tube 150 into the cuvette 153 held in the holding portion 24a of the primary dispensation table 24 while sampling part of the specimen sampled into the cuvette 153 held in the holding portion 24a of the primary dispensation table 24 into the cuvette 154 held in the holding portion 23a of the secondary dispensation table 23, whereby only part of the specimen sampled into the cuvette 153 may be sampled into the cuvette 154 so that the specimen stored in the test tube 150 may not be sampled in measurement or remeasurement with the second optical information acquisition portion 70. Thus, the test tube 150 from which the specimen has been sampled may not be put on standby around the specimen analyzing apparatus 1, whereby the degree of freedom in handling of the test tube 150 from which the sample has been sampled can be improved.

According to the first embodiment, the control portion 4b of the control unit 4 determining whether or not the specimen in the cuvette 153 held in the holding portion 24a of the primary dispensation table 24 is the object of secondary dispensation on the basis of the analysis results of the optical information acquired by the first optical information acquisition portion 40 is so provided that the second optical information acquisition portion 70 acquires optical information only when correct analysis can be performed in the second optical information acquisition portion 70. Thus, no useless analysis may be performed, whereby analytical efficiency can be inhibited from reduction.

According to the first embodiment, the specimen is sucked from the test tube 150 by passing the nozzle 35 of the specimen dispensation arm 30 through the recess portion 152a of the lid 152 while the specimen analyzing apparatus 1 samples the specimen from the cuvette 153 held in the holding portion 24a of the primary dispensation table 24 into the cuvette 154 held in the holding portion 23a of the secondary dispensation table 23 and reanalyzes the specimen sampled into the cuvette 154 when it is necessary to reanalyze the same specimen, whereby the nozzle 35 may not be passed through the lid 152 of the test tube 150 at the time of the reanalysis. Thus, fragments of the lid 152 of the test tube 150 can be inhibited from entering the test tube 150 or clogging the nozzle 35 due to the operation of repassing the nozzle 35 through the lid 152 of the test tube 150, whereby precision in the quantity of suction can be inhibited from reduction when the specimen is sucked from the test tube 150 by the prescribed constant quantity.

According to the first embodiment, the lamp portion 73 emitting the lights having the five different wavelengths is so provided that the lamp portion 73 can apply the lights having the five different wavelengths to the measurement sample, whereby a plurality of types of electric signals can be obtained through the photoelectric conversion element 74 and the A/D converter 77. Thus, the optical information can be easily acquired from the measurement sample under a plurality of conditions.

According to the first embodiment, the amplification portion 76 including the amplifier (L) 76a having the prescribed gain (amplification factor), the amplifier (H) 76b having the higher gain (amplification factor) than the amplifier (L) 76a and the changeover switch 76c selecting whether to output the electric signals received from the amplifier (H) 76b to the A/D converter 77 or to output the electric signals received from the amplifier (H) 76b to the A/D converter 77 is so provided that the electric signals converted by the photoelectric conversion element 74 can be input in and amplified by the amplifier (L) 76a and the amplifier (H) 76b having different amplification factors. Thus, a plurality of types of electric signals can be obtained through the A/D converter 77, whereby the optical information can be easily acquired from the measurement sample under a plurality of conditions.

Second Embodiment

Referring to FIGS. 17 to 27, a specimen analyzing apparatus 201 comprising a lamp unit 250 employed in common for a first optical information acquisition portion 240 and a second optical information acquisition portion 270 dissimilarly to the aforementioned first embodiment is described in this second embodiment. A coagulation time method employed in the second embodiment is a measuring method detecting the process of coagulation of a specimen as a change of transmitted light. As measurement items subjected to measurement with the coagulation time method, there are PT (prothrombin time), APTT (activated partial thromboplastin time), Fbg (fibrinogen quantity) and the like.

Figure 17:
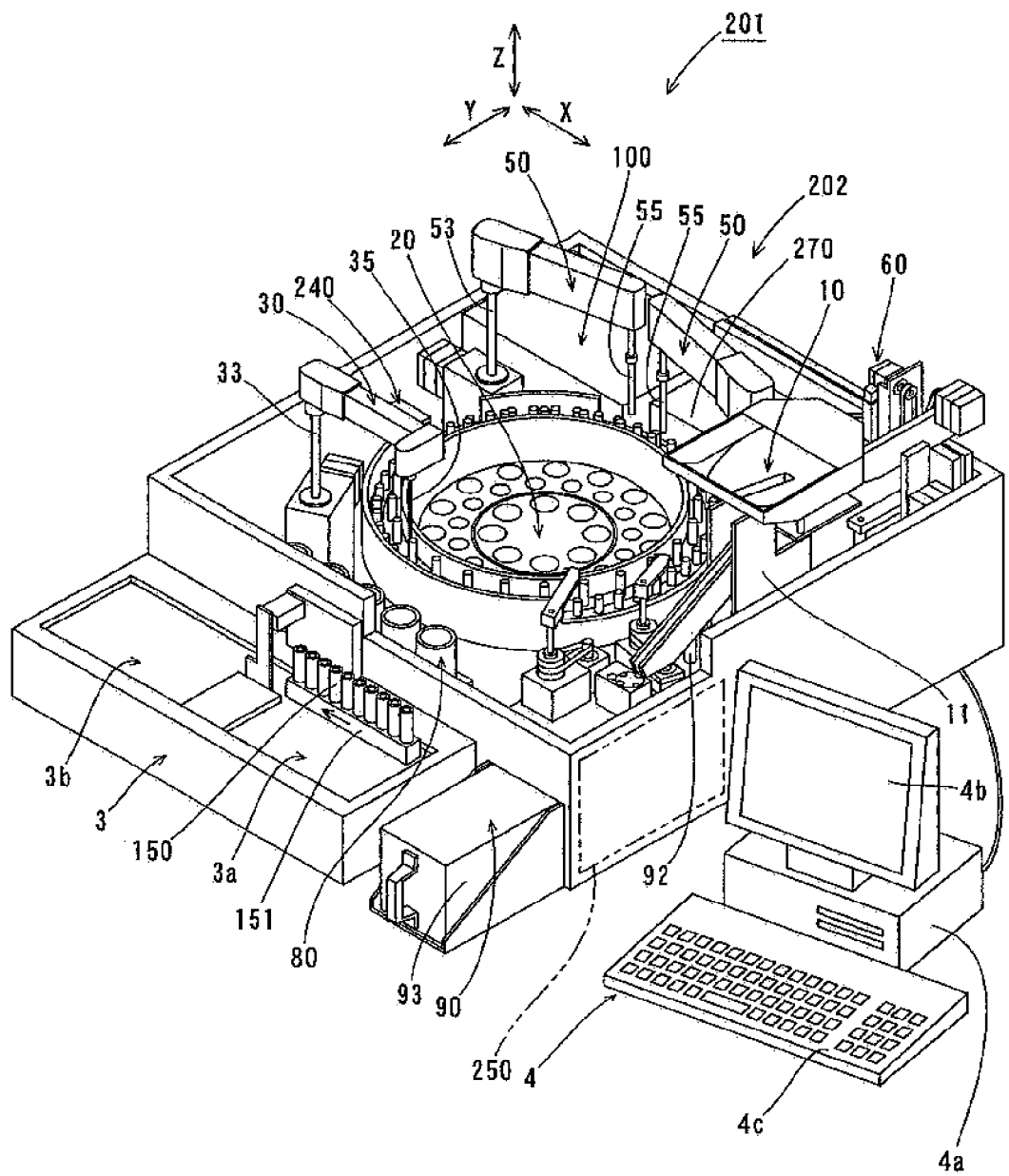
FIG. 17 is a perspective view showing the overall structure of a specimen analyzing apparatus according to a second embodiment of the present invention.

The specimen analyzing apparatus 201 is constituted of a detection mechanism portion 202, a transport mechanism portion 3 arranged on the front side of the detection mechanism portion 202 and a control unit 4 electrically connected to the detection mechanism portion 202, as shown in FIG. 17. The transport mechanism portion 3 and the control unit 4 of the specimen analyzing apparatus 201 according to the second embodiment are similar in structure to those of the aforementioned first embodiment, and hence redundant description thereof is omitted.

Figure 18:
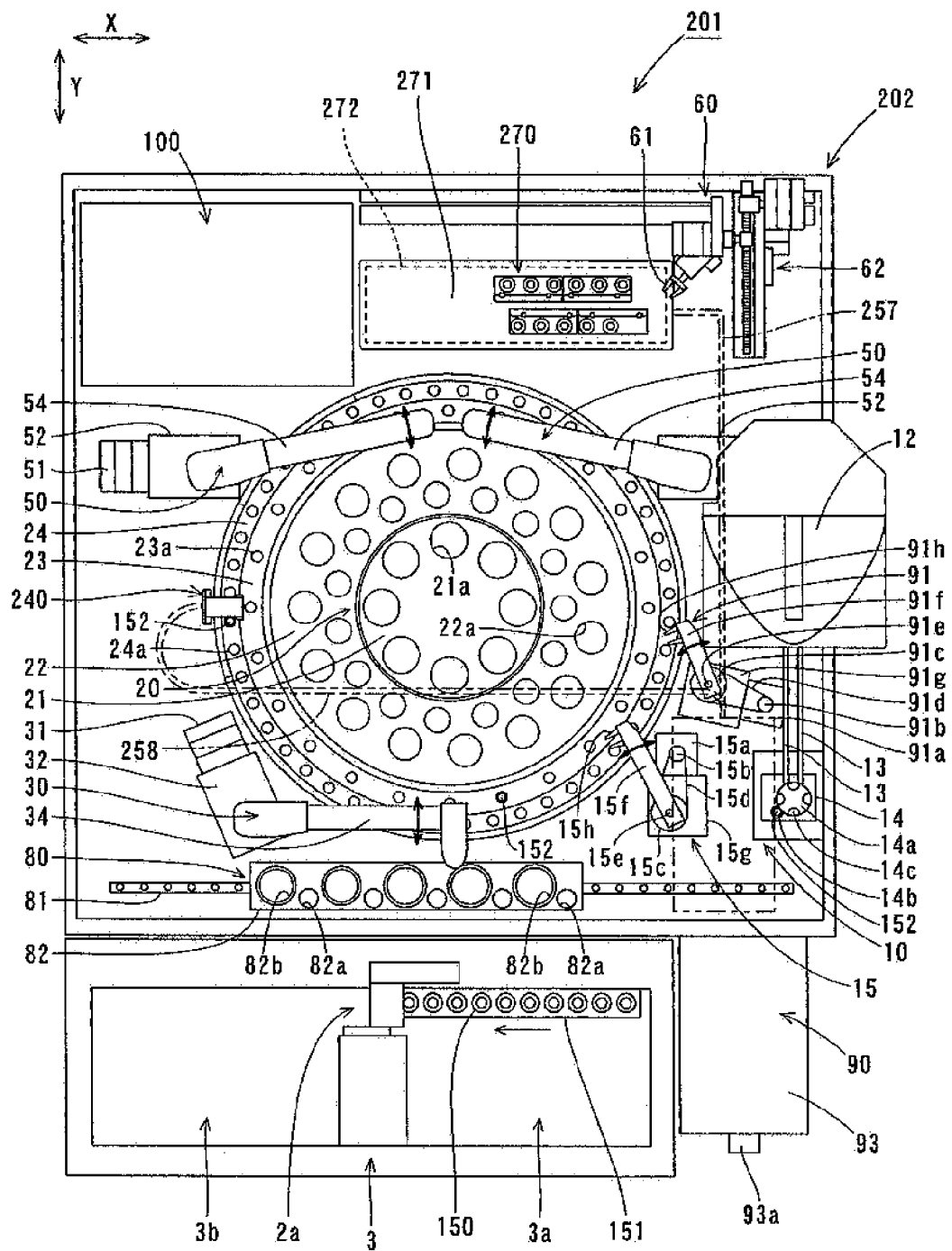
FIG. 18 is a plan view showing a detection mechanism portion and a transport mechanism portion of the specimen analyzing apparatus according to the second embodiment shown in FIG. 17.

The detection mechanism portion 202 according to this second embodiment comprises a cuvette supply portion 10, a rotational transport portion 20, a specimen dispensation arm 30, the first optical information acquisition portion 240, the lamp unit 250, two reagent dispensation arms 50, a cuvette transfer portion 60, the second optical information acquisition portion 270, an emergency specimen set portion 80, a cuvette disposal portion 90 and a fluid portion 100, as shown in FIGS. 17 and 18. The structures of the cuvette supply portion 10, the rotational transport portion 20, the specimen dispensation arm 30, the reagent dispensation arms 50, the cuvette transfer portion 60, the emergency specimen set portion 80, the cuvette disposal portion 90 and the fluid portion 100 of the detection mechanism portion 202 according to the second embodiment are similar the structures of those of the detection mechanism portion 2 according to the aforementioned first embodiment.

The first optical information acquisition portion 240 is so formed as to acquire optical information from each specimen, in order to measure presence/absence of interference substances (chyle, hemoglobin and bilirubin) in the specimen and concentrations thereof before addition of reagents. More specifically, the first optical information acquisition portion 240 measures presence/absence of the interference substances and the concentrations thereof with four types of lights (405 nm, 575 nm, 660 nm and 800 nm) among five types of lights (340 nm, 405 nm, 575 nm, 660 nm and 800 nm) emitted from the lamp unit 250 described later.

Figure 19:
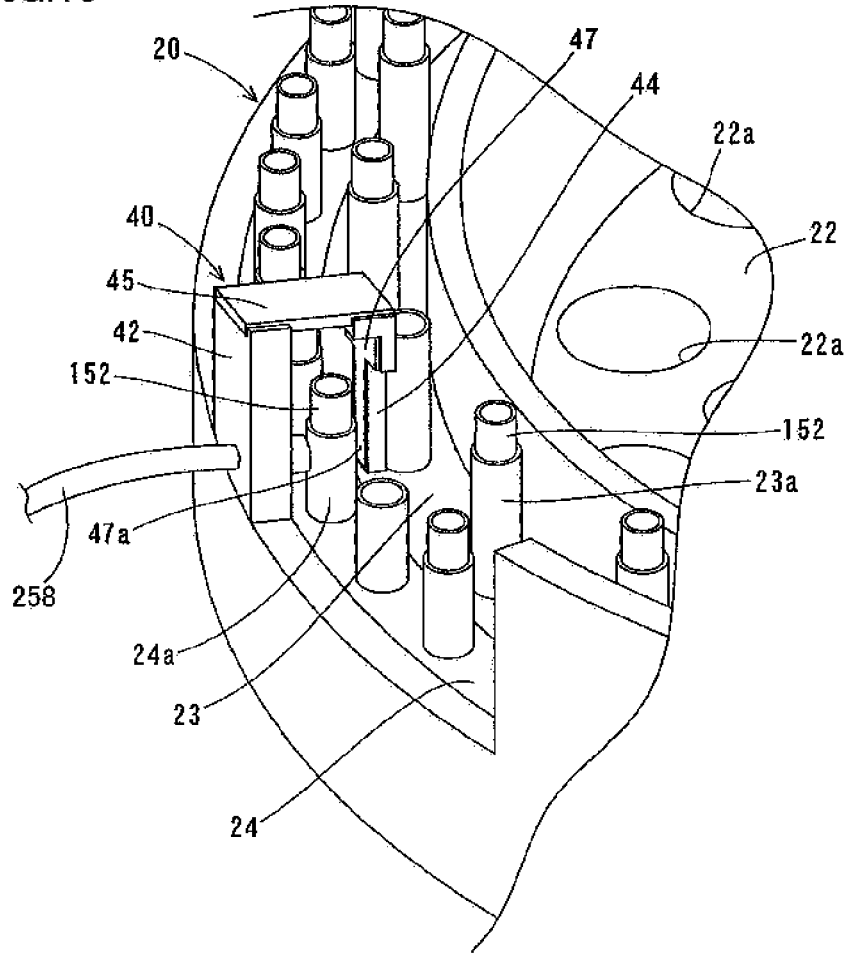
FIG. 19 is a perspective view showing a first optical information acquisition portion of the specimen analyzing apparatus according to the second embodiment shown in FIG. 17.
Figure 20:
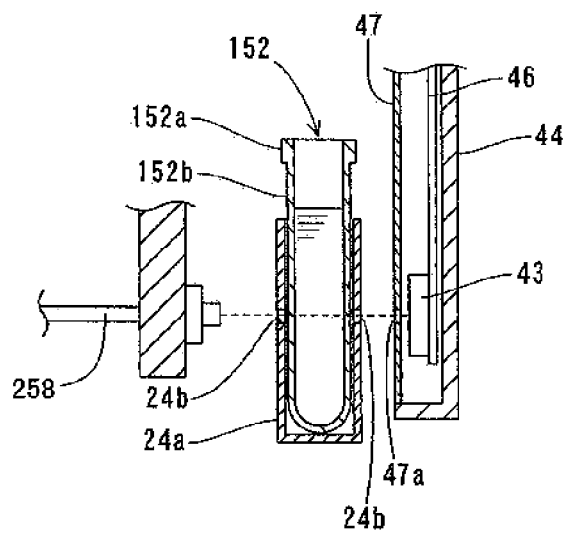
FIG. 20 is a schematic diagram for illustrating the structure of the first optical information acquisition portion of the specimen analyzing apparatus according to the second embodiment shown in FIG. 17.
Figure 21:
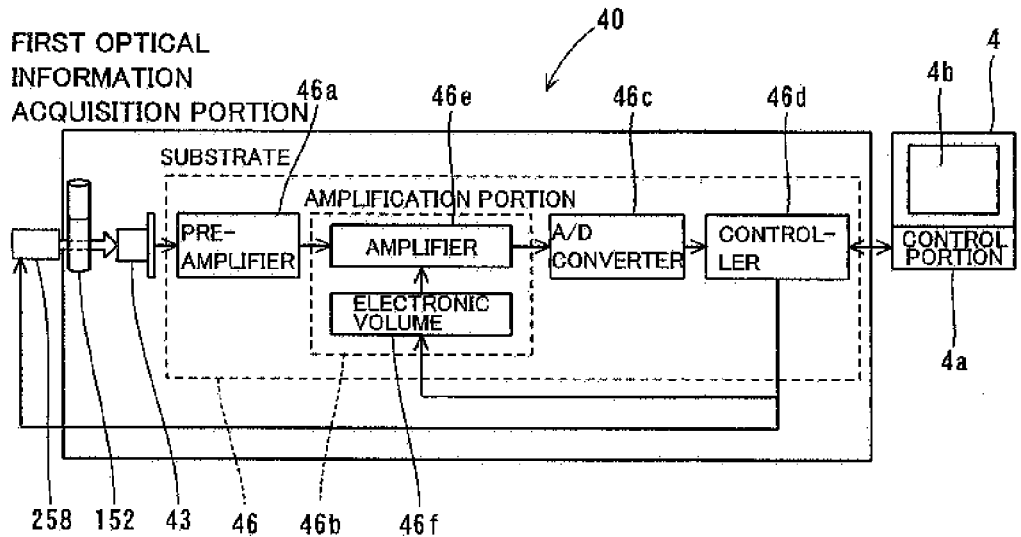
FIG. 21 is a block diagram of the first optical information acquisition portion of the specimen analyzing apparatus according to the second embodiment shown in FIG. 17.

In the first optical information acquisition portion 240 according to the second embodiment, a branched optical fiber 258 of the lamp unit 250 described later is guided as shown in FIGS. 19 and 20, dissimilarly to the light-emitting diode (LED) 41 (see FIG. 5) of the first optical information acquisition portion 40 according to the first embodiment. The five types of lights applied from the branched optical fiber 258 are applied to the specimen stored in a cuvette 152 held in each holding portion 24a of a primary dispensation table 24, to be transmitted through the specimen stored in this cuvette 152 and thereafter detected by a photoelectric conversion element 43 through a slit 47a of a lid member 47. As shown in FIG. 21, electric signals generated in the photoelectric conversion element 43 are converted to digital signals by an A/D converter 46c, and transmitted to the control portion 4a of the control unit 4. The control portion 4a of the control unit 4 obtains the absorbance and analyzes presence/absence of the interference substances in the specimen and the concentrations thereof with the received digital signals. According to the second embodiment, whether or not to analyze optical information measured in the second optical information acquisition portion 270 described later is determined on the basis of presence/absence of the interference substances in the specimen and the concentrations thereof.

According to the second embodiment, the lamp unit 250 is provided for supplying the lights employed for optical measurement performed in the first optical information acquisition portion 240 and the second optical information acquisition portion 270, as shown in FIG. 18. In other words, the single lamp unit 250 is formed to be employed in common for the first optical information acquisition portion 240 and the second optical information acquisition portion 270. This lamp unit 250 is constituted of a halogen lamp 251 serving as a light source, condensing lenses 252a to 252c, a discoidal filter portion 253, a motor 254, a light transmission type sensor 255, an optical fiber coupler 256, 11 branched optical fibers 257 (see FIG. 23) and the single branched optical fiber 258 (see FIG. 23), as shown in FIGS. 22 and 23.

Figure 22:
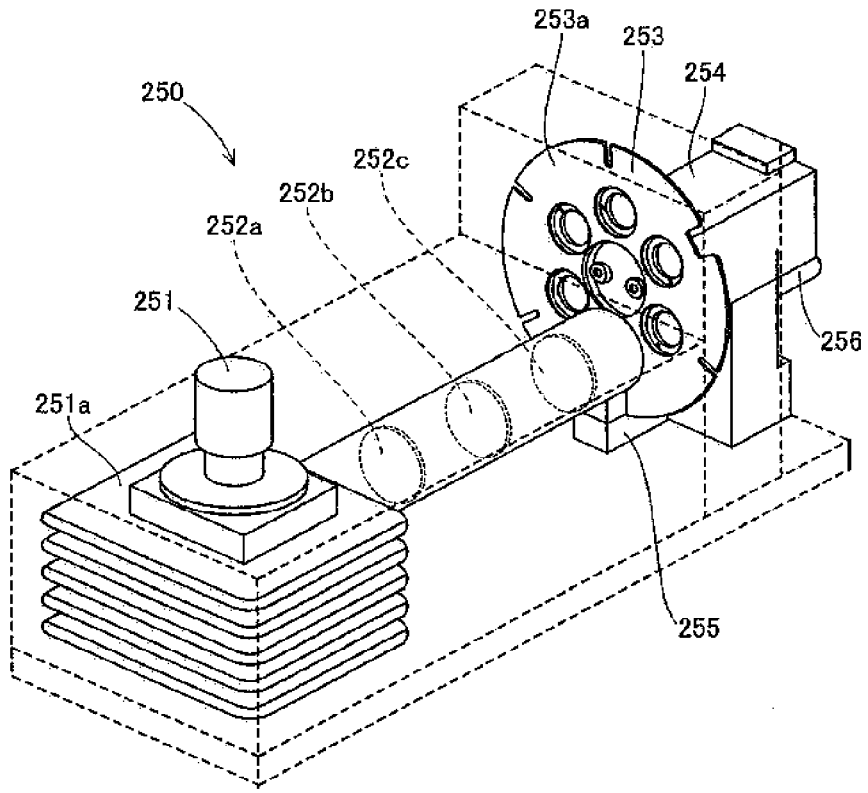
FIG. 22 is a perspective view showing a lamp unit of the specimen analyzing apparatus according to the second embodiment shown in FIG. 17.
Figure 23:
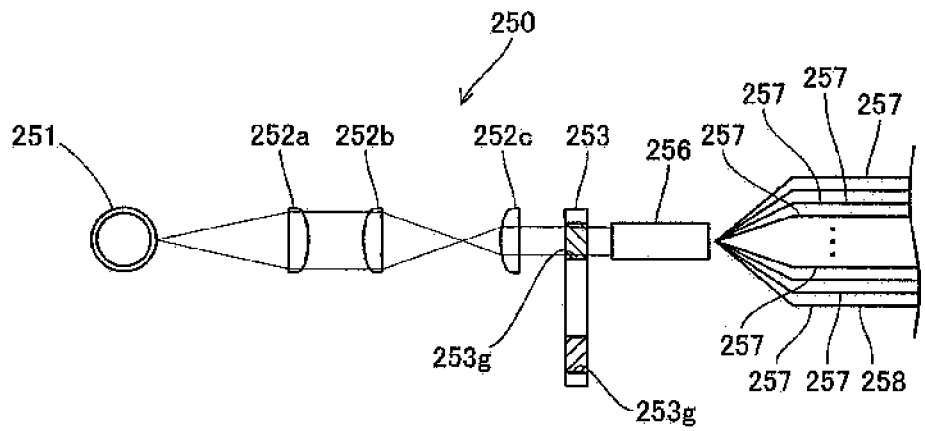
FIG. 23 is a schematic diagram for illustrating the structure of the lamp unit of the specimen analyzing apparatus according to the second embodiment shown in FIG. 17.

The halogen lamp 251 is stored in a lamp case 251a having a plurality of fins for cooling the air heated by heat generation of the halogen lamp 251, as shown in FIG. 22.

The condensing lenses 252a to 252c have a function of condensing lights emitted from the halogen lamp 251. The condensing lenses 252a to 252c are arranged on optical paths guiding the lights emitted from the halogen lamp 251 to the optical fiber coupler 256. The lights emitted from the halogen lamp 251 and condensed by the condensing lenses 252a to 252c are transmitted through any one of optical filters 253b to 253f of the filter portion 253 described later and guided to the optical fiber coupler 256.

Figure 24:
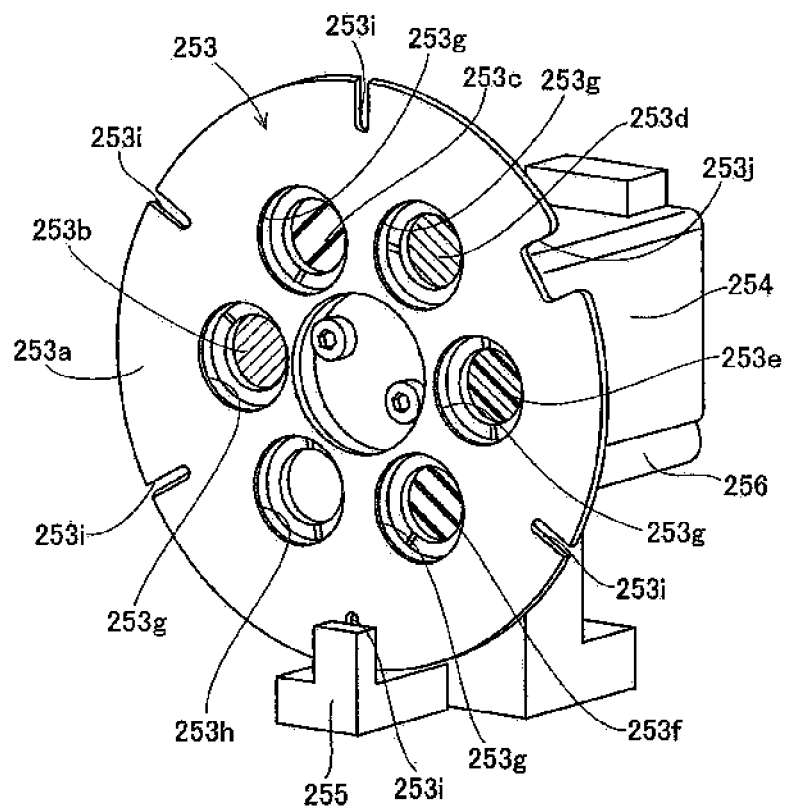
FIG. 24 is an enlarged perspective view showing a filter portion of the lamp unit shown in FIG. 22.

The filter portion 253 of the lamp unit 250 is mounted to be rotatable about the motor shaft (not shown) of the motor 254, as shown in FIG. 24. This filter portion 253 includes a filter plate 253a provided with the five optical filters 253b to 253f having different light transmission characteristics (transmission wavelengths) respectively. The filter plate 253a is provided with five holes 253g for mounting the optical filters 253b to 253f and a hole 253h so blocked up as not to transmit any light. The five optical filters 253b, 253c, 253d, 253e and 253f having different light transmission characteristics (transmission wavelengths) are set in the five holes 253g respectively. These holes 253g and 253h are provided at prescribed angular intervals (regular intervals of 60° in the second embodiment) along the rotational direction of the filter portion 253. The hole 253h is a preliminary hole, and mounted with a filter when addition of the filter is necessary.

The optical filters 253b, 253c, 253d, 253e and 253f transmit the lights having the wavelengths of 340 nm, 405 nm, 575 nm, 660 nm and 800 nm respectively, and do not transmit lights of other wavelengths. Therefore, lights transmitted through the optical filters 253b, 253c, 253d, 253e and 253f have the wavelength characteristics of 340 nm, 405 nm, 575 nm, 660 nm and 800 nm respectively.

Further, the filter plate 253a is provided with six slits at prescribed angular intervals (regular intervals of 60° in the second embodiment) along the circumferential direction. One of these six slits is an origin slit 253j having a larger slit width than the remaining five normal slits 253i in the rotational direction of the filter plate 253a. The origin slit 253j and the normal slits 253i are formed on intermediate angle positions between the adjacent holes 253g and 253h at prescribed angular intervals (regular intervals of 60° in the second embodiment).

According to the second embodiment, the filter portion 253 is so formed as to continuously rotate when the lamp unit 250 applies the lights to each cuvette 152 of the primary dispensation table 24. Following the rotation of the filter plate 253a, therefore, the five optical filters 253b to 253f having different light transmission characteristics and the single shielded hole 253h (see FIG. 21) are intermittently successively arranged on the optical paths of the lights condensed by the condensing lenses 252a to 252c (see FIG. 20). Therefore, the five types of lights having different wavelength characteristics are intermittently successively applied.

The light transmission type sensor 255 is provided for detecting passage of the origin slit 253j and the normal slits 253i following the rotation of the filter portion 253, as shown in FIG. 24. When the origin slit 253j and the normal slits 253i pass this sensor 255, a photoreceiving portion detects the lights from the light source through the slits and outputs detection signals. The origin slit 253j has the larger slit width than the normal slits 253i, whereby the detection signal output from the sensor 255 upon passage of the origin slit 253j has a longer output period than the detection signals output upon passage of the normal slits 253i. Therefore, it is possible to monitor whether or not the filter portion 253 normally rotates on the basis of the detection signals received from the sensor 255.

Figure 25:
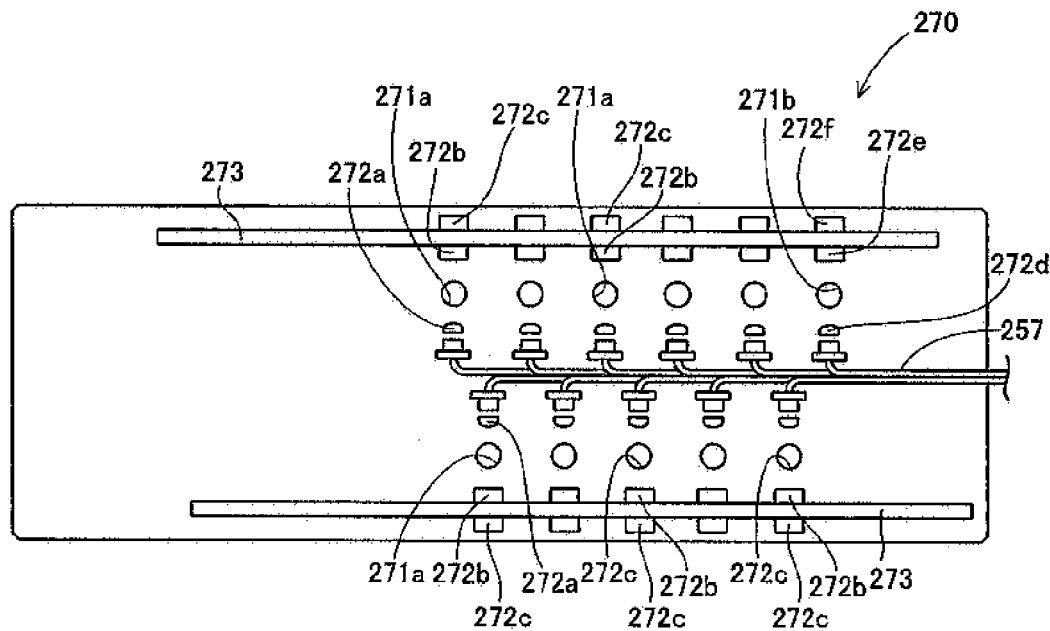
FIG. 25 is a schematic diagram for illustrating the internal structure of a detection portion of a second optical information acquisition portion of the specimen analyzing apparatus according to the second embodiment shown in FIG. 17.

The optical fiber coupler 256 has a function of introducing the lights, passed through the optical filters 253b to 253f, into the respective ones of the 11 branched optical fibers 257 and the single branched optical fiber 258. In other words, the optical fiber coupler 256 simultaneously guides homogeneous lights to the 11 branched optical fibers 257 and the single branched optical fiber 258. The forward ends of the 11 branched optical fibers 257 are connected to the second optical information acquisition portion 270 as shown in FIG. 18, for guiding the lights received from the lamp unit 250 to a measurement sample stored in each cuvette 152 set on the second optical information acquisition portion 270. More specifically, the 11 branched optical fibers 257 are so arranged as to supply the lights to 10 insertion holes 271a and one reference light measuring hole 271b, described later, of the second optical information acquisition portion 270 respectively, as shown in FIG. 25. The forward end of the single branched optical fiber 258 is connected to the first optical information acquisition portion 240 as shown in FIGS. 18 and 19 dissimilarly to the 11 branched optical fibers 257, for guiding the lights received from the lamp unit 250 to the specimen stored in the cuvette 152 held in the holding portion 24a of the primary dispensation table 24. Therefore, the five types of lights having different wavelength characteristics, intermittently passed through the optical filters 253b to 253f, are supplied to the respective ones of the first optical information acquisition portion 240 and the second optical information acquisition portion 270 through the branched optical fibers 257 and 258.

The second optical information acquisition portion 270 has a function for heating the measurement sample prepared by adding reagents to the specimen and measuring optical information from the measurement sample. This second optical information acquisition portion 270 is constituted of a cuvette receiving portion 271 and a detection portion 272 arranged under the cuvette receiving portion 271, as shown in FIG. 18. The cuvette receiving portion 271 is provided with the 10 insertion holes 271a for inserting the cuvettes 152 (see FIG. 18) and the single reference light measuring hole 271b for measuring a reference light without receiving any cuvette 152, as shown in FIG. 25. Further, the cuvette receiving portion 271 stores a heating mechanism (not shown) for heating the cuvettes 152 inserted into the insertion holes 271a to a prescribed temperature.

According to the second embodiment, the reference light measuring hole 271b is provided for monitoring the characteristics of the lights applied from the branched optical fibers 257. More specifically, the reference light measuring hole 271b introduces the lights applied from the branched optical fibers 257 directly into a reference light photoelectric conversion element 272e of the detection portion 272, thereby detecting characteristics such as fluctuation derived from the halogen lamp 251 (see FIG. 22) of the lamp unit 250 as electric signals. The detected characteristics (electric signals) of the lights are subtracted from signals corresponding to lights transmitted through the measurement sample stored in each cuvette 152 inserted into the corresponding insertion hole 271a, thereby correcting the signals corresponding to the lights transmitted through the measurement sample. Thus, occurrence of small differences resulting from the characteristics of the lights can be suppressed every measurement of optical information.

The detection portion 272 of the second optical information acquisition portion 270 is enabled to perform optical measurement (main measurement) on the measurement sample stored in the cuvette 152 inserted into the insertion hole 271a under a plurality of conditions. This detection portion 272 is provided with collimator lenses 272a, photoelectric conversion elements 272b and preamplifiers 272c correspondingly to the respective insertion holes 271a into which the cuvettes 152 are inserted, and provided with a reference light collimator lens 272d, a reference light photoelectric conversion element 272e and a reference light preamplifier 272f correspondingly to the reference light measuring hole 271b (see FIG. 25), as shown in FIGS. 25 and 26.

Figure 26:
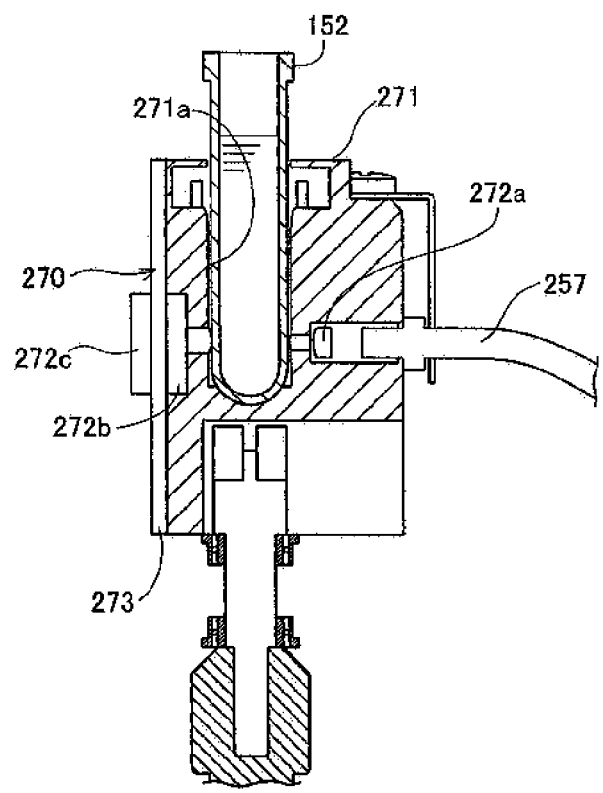
FIG. 26 is a sectional view for illustrating the structure of the detection portion of the second optical information acquisition portion of the specimen analyzing apparatus according to the second embodiment shown in FIG. 17.

The collimator lenses 272a are set between ends of the branched optical fibers 257 inducing the lights received from the lamp unit 250 (see FIG. 22) and the corresponding insertion holes 271a, as shown in FIGS. 25 and 26. These collimator lenses 272a are provided for parallelizing the lights applied from the branched optical fibers 257. The photoelectric conversion elements 272b are mounted on surfaces of substrates 273, opposed to ends of the branched optical fibers 257 through the insertion holes 271a, closer to the insertion holes 271a. The photoelectric conversion elements 272b have a function of detecting the lights (hereinafter referred to as transmitted lights) transmitted through the measurement samples when the lights are applied to the measurement samples stored in the cuvettes 152 inserted into the insertion holes 271a and outputting electric signals (analog signals) corresponding to the detected transmitted lights. These photoelectric conversion elements 272b are so arranged as to receive the five types of lights applied from the branched optical fibers 257 of the lamp unit 250. The light having the wavelength of 405 nm applied from the branched optical fibers 257 is a main wavelength employed for measuring Fbg (fibrinogen quantity). The light having the wavelength of 660 nm is a main wavelength employed for measuring PT (prothrombin time) and APTT (activated partial thromboplastin time), and also a sub wavelength employed for measuring Fbg. The light having the wavelength of 800 nm is a sub wavelength employed for measuring PT and APTT.

The preamplifiers 272c are mounted on surfaces of the substrates 273 opposite to the insertion holes 271a, and provided for amplifying the electric signals (analog signals) received from the photoelectric conversion elements 272b.

Figure 27:
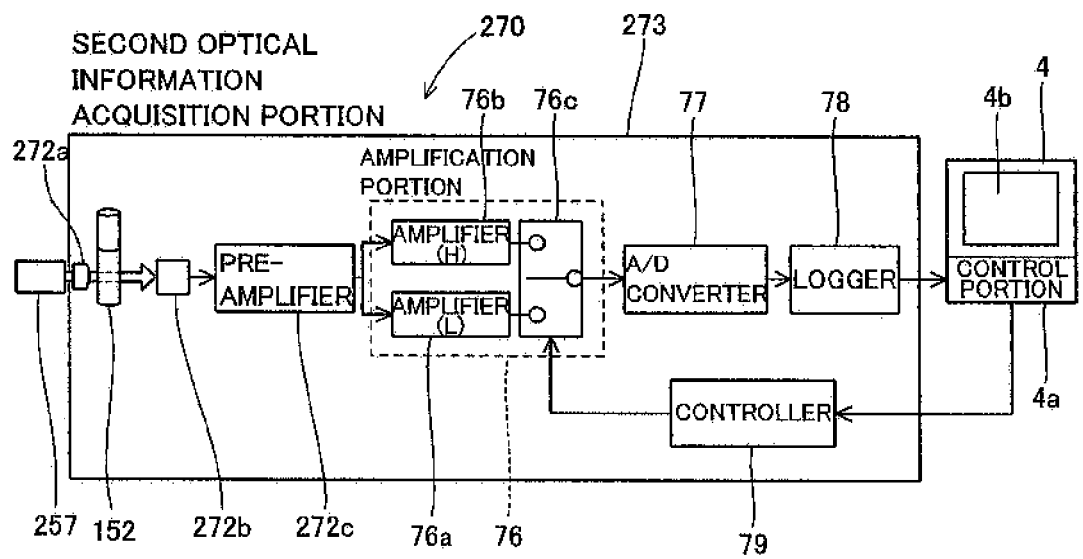
FIG. 27 is a block diagram of the second optical information acquisition portion of the specimen analyzing apparatus according to the second embodiment shown in FIG. 17.

Each substrate 273 is provided with an amplification portion 76, an A/D converter 77, a logger 78 and a controller 79 in addition to the aforementioned photoelectric conversion elements 272b (reference light photoelectric conversion element 272e) and the preamplifiers 272c (reference light preamplifier 272f), as shown in FIG. 27. The amplification portion 76 includes an amplifier (L) 76a having a prescribed gain (amplification factor), an amplifier (H) 76b having a higher gain (amplification factor) than the amplifier (L) 76a and a changeover switch 76c.

Figure 28:
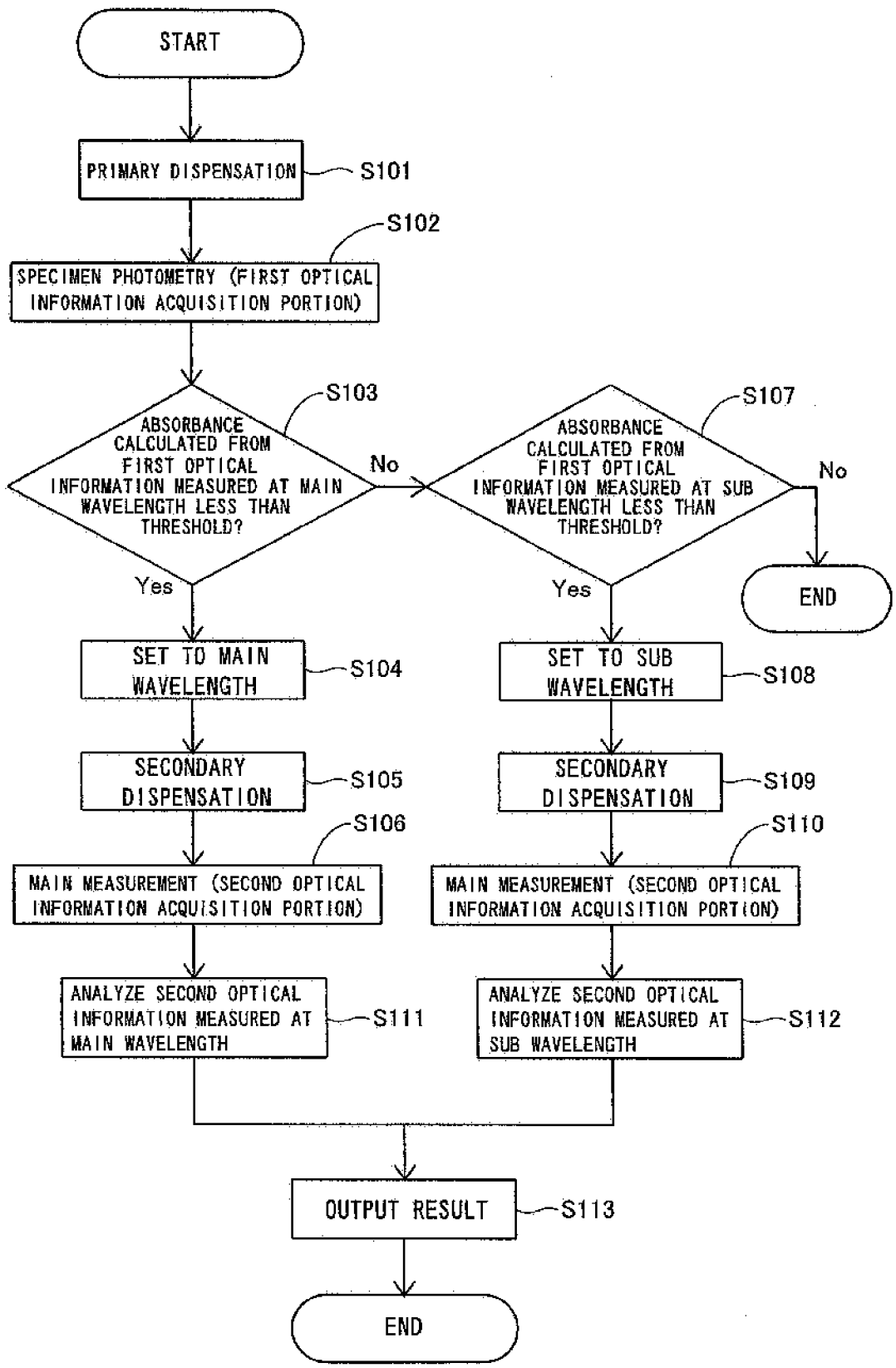
FIG. 28 is a flow chart showing the procedure of a specimen analyzing operation of the specimen analyzing apparatus according to the second embodiment shown in FIG. 17.

FIG. 28 is a flow chart showing the procedure of a specimen analyzing operation of the specimen analyzing apparatus according to the second embodiment shown in FIG. 17. The specimen analyzing operation of the specimen analyzing apparatus 201 is now described in detail with reference to FIGS. 17 to 21, 22, 24, 26 and 28.

First, the power sources of the detection mechanism portion 202 and the control unit 4 of the specimen analyzing apparatus 201 shown in FIG. 17 are brought into ON-states respectively, thereby initializing the specimen analyzing apparatus 201. Thus, an operation for returning a mechanism for moving each cuvette 152 and the respective dispensation arms to initial positions, initialization of software stored in the control portion 4a of the control unit 4 etc. are performed.

The transport mechanism portion 3 shown in FIG. 18 transports a rack 151 receiving test tubes 150 storing the specimens. Thus, the rack 151 of a rack set region 3a is transported to a position corresponding to a suctional position 2a of the detection mechanism portion 202.

At a step S101, the specimen dispensation arm 30 sucks a prescribed quantity of specimen from each test tube 150. Then, the specimen dispensation arm 30 is moved to a position above the corresponding cuvette 152 held on the primary dispensation table 24 of the rotational transport portion 20. Thereafter the specimen dispensation arm 30 discharges the specimen into the cuvette 152 of the primary dispensation table 24, so that the specimen is sampled into the cuvette 152.

The primary dispensation table 24 is rotated for transporting the cuvette 152 into which the specimen has been dispensed to a position allowing measurement with the first optical information acquisition portion 240. Thus, the first optical information acquisition portion 240 optically measures the specimen and acquires optical information from the specimen at a step S102. More specifically, the photoelectric conversion element 43 successively detects the five types (340 nm, 405 nm, 575 nm, 660 nm and 800 nm) of lights transmitted through the specimen stored in the cuvette 152 held in each holding portion 24a (see FIG. 20) of the primary dispensation table 24. A preamplifier 45a (see FIG. 21) and an amplifier 45e amplify the electric signals detected by the photoelectric conversion element 43, while the A/D converter 45c converts the same to digital signals. Thereafter a controller 45d transmits the data of the digital signals to the control portion 4a of the control unit 4. Thus, the first optical information acquisition portion 240 completes acquisition of optical information (first optical information) with respect to the specimen.

After the acquisition of the optical information (first optical information) at the step S102, a CPU 401a determines whether or not an absorbance at the main wavelength calculated from the first optical information measured in the first optical information acquisition portion 240 is less than a threshold at a step S103. More specifically, if the inspection item of the specimen is "PT", a determination is made as to whether or not an absorbance calculated from first optical information measured by applying the light having 660 nm which is the main wavelength for "PT" is less than a threshold (2.0, for example). Similarly, if the inspection item of the specimen is "APTT", a determination is made as to whether or not an absorbance calculated from first optical information measured by applying the light having 660 nm which is the main wavelength for "APTT" is less than a threshold (2.0, for example). If the inspection item of the specimen is "ATIII", a determination is made as to whether or not an absorbance calculated from first optical information measured by applying the light having 405 nm which is the main wavelength for "ATIII" is less than a threshold (2.0, for example).

If the absorbance at the main wavelength calculated from the first optical information measured in the first optical information acquisition portion 240 is less than the threshold at the step S103, the CPU 401a sets an analytic wavelength for analyzing second optical information to the main wavelength at a step S104. At a step S105, the specimen dispensation arm 30 sucks a prescribed quantity of the specimen from the cuvette 152 held in the holding portion 24a of the primary dispensation table 24. Thereafter the specimen dispensation arm 30 discharges the prescribed quantity of the specimen into a plurality of cuvettes 152 of the secondary dispensation table 23 respectively, so that secondary dispensation processing is performed. Then, the reagent dispensation arms 50 are driven for adding reagents stored in reagent containers (not shown) placed on reagent tables 21 and 22 to the specimens stored in the cuvettes 152 of the secondary dispensation table 23. Thus, measurement samples are prepared. Then, the cuvettes 152 of the secondary dispensation table 23 storing the measurement samples are moved into the insertion holes 271a of the cuvette receiving portion 271 of the second optical information acquisition portion 270 with the cuvette transfer portion 60.

At a step S106, the detection portion 272 of the second optical information acquisition portion 270 performs optical measurement (main measurement) on the measurement sample in each cuvette 152 under a plurality of conditions, thereby acquiring a plurality (10 types) of optical information (second optical information) from the measurement sample. More specifically, the cuvette 152 inserted into the insertion hole 271a of the cuvette receiving portion 271 is heated by the heating mechanism (not shown) to the prescribed temperature. Thereafter each branched optical fiber 257 of the lamp unit 250 applies lights to the cuvette 152 of the cuvette receiving portion 271, as shown in FIG. 26. The branched optical fiber 257 periodically applies lights of five different wavelengths (340 nm, 405 nm, 575 nm, 660 nm and 800 nm) due to the rotation of the filter portion 253 (see FIG. 24). The lights of the aforementioned respective wavelengths applied from the branched optical fiber 257 and transmitted through the cuvette 152 and the measurement sample stored in the cuvette 152 are successively detected by the corresponding photoelectric conversion element 272b. Electric signals corresponding to the lights of five different wavelengths converted by the photoelectric conversion element 272b are amplified by the corresponding preamplifier 272c, and thereafter successively input in the amplification portion 76.

In the amplification portion 76, the electric signals corresponding to the lights of five different wavelengths received from the preamplifier 272c (see FIG. 27) are input in the amplifier (H) 76b having the high amplification factor and the amplifier (L) 76a having the normal amplification factor respectively. The controller 79 controls the changeover switch 76c, so that the electric signals amplified by the amplifier (H) 76b are output to the A/D converter 77, and the electric signals amplified by the amplifier (L) 76a are thereafter output to the A/D converter 77. The changeover switch 76c is repetitively switched in response to the timing of rotation of the filter portion 253 (see FIG. 24) in the lamp unit 250. Thus, the amplification portion 76 amplifies the electric signals corresponding to the lights of five different wavelengths with two different amplification factors respectively, and repetitively outputs 10 types of electric signals in total to the A/D converter 77. The 10 types of electric signals are converted to digital signals by the A/D converter 77, temporarily stored in the logger 78, and thereafter successively transmitted to the control portion 4a of the control unit 4. Thus, the second optical information acquisition portion 270 completes acquisition of the plurality (10 types) of optical information (second optical information) with respect to the measurement sample.

If the absorbance at the main wavelength calculated from the first optical information measured in the first optical information acquisition portion 240 is greater than the threshold at the step S103, on the other hand, the CPU 401a determines whether or not an absorbance at the sub wavelength calculated from the first optical information measured in the first optical information acquisition portion 240 is less than a threshold at a step S107. More specifically, if the inspection item of the specimen is "PT", a determination is made as to whether or not an absorbance calculated from the first optical information measured by applying the light having 800 nm which is the sub wavelength for "PT" is less than a threshold (2.0, for example). Similarly, if the inspection item of the specimen is "APTT", a determination is made as to whether or not an absorbance calculated from the first optical information measured by applying the light having 800 nm which is the sub wavelength for "APTT" is less than a threshold (2.0, for example). If the inspection item of the specimen is "ATIII", a determination is made as to whether or not an absorbance calculated from the first optical information measured by applying the light having 660 nm which is the sub wavelength for "ATIII" is less than a threshold (2.0, for example).

If the absorbance at the sub wavelength calculated from the first optical information measured in the first optical information acquisition portion 240 is less than the threshold at the step S107, the CPU 401a sets the analytic wavelength for analyzing the second optical information to the sub wavelength at a step S108. At steps S109 and S110, the second optical information acquisition portion 270 acquires a plurality (10 types) of optical information (second optical information) with respect to the measurement sample, similarly to the aforementioned steps S105 and S106.

If the absorbance at the sub wavelength calculated from the first optical information measured in the first optical information acquisition portion 240 is greater than the threshold at the step S107, on the other hand, the CPU 401a determines that it is difficult to perform reliable analysis due to remarkable influences by interference substances (bilirubin, hemoglobin and chyle) contained in the specimen, for stopping the main measurement and terminating the processing. Thus, no reagents are added to an unanalyzable specimen remarkably influenced by the interference substances for preparing a measurement sample, whereby the reagents can be inhibited from wasting. As a case where it is difficult to perform reliable measurement (case of stopping the main measurement), a case where the lights transmitted through the specimen are blocked due to presence of large quantities of interference substances in the specimen detected by the first optical information acquisition portion 240 and the transmitted lights transmitted through the specimen cannot be substantially detected or the like can be listed.

After the acquisition of the second optical information (main measurement) with the second optical information acquisition portion 270 at the aforementioned step S106, second optical information of the measurement sample measured at the main wavelength set to the analytic wavelength is transmitted to the control portion 4a of the control unit 4 from among the plurality of second optical information measured in the second optical information acquisition portion 270 and analyzed by the CPU 401a at a step S111. If the inspection item of the specimen is "PT", for example, the second optical information measured by applying the light having 660 nm which is the main wavelength for "PT" is first transmitted to the control portion 4a of the control unit 4. Thereafter the CPU 401a receiving the second optical information acquired at the main wavelength outputs analysis results on the basis of the second optical information.

Similarly, after the acquisition of the second optical information (main measurement) with the second optical information acquisition portion 270 at the aforementioned step S110, second optical information of the measurement sample measured at the sub wavelength set to the analytic wavelength is transmitted to the control portion 4a of the control unit 4 from among the plurality of second optical information measured in the second optical information acquisition portion 270 and analyzed by the CPU 401a at a step S112. More specifically, if the inspection item of the specimen is "PT", second optical information measured by applying the light having 800 nm which is the sub wavelength for "PT" is first transmitted to the control portion 4a of the control unit 4. Thereafter the CPU 401a receiving the second optical information acquired at the sub wavelength outputs analysis results on the basis of the second optical information.

After the analysis with the CPU 401a of the control unit 4 at the steps S111 and S112 is completed, the CPU 401a displays the analysis results obtained at the aforementioned step S111 or the step S112 on a display portion 4b of the control unit 4 at a step S113. Thus, the specimen analyzing operation of the specimen analyzing apparatus 201 is terminated.

Qualitative determination related to interference substances is now described. The control portion 4a of the control unit 4 calculates the absorbance of the specimen with the data (first optical information) of the received digital signals, and calculates presence/absence of interference substances (chyle, hemoglobin and bilirubin) in the specimen and concentrations thereof. More specifically, the control portion 4a of the control unit 4 calculates the absorbance of the specimen and calculates presence/absence of interference substances (chyle, hemoglobin and bilirubin) and concentrations thereof on the basis of optical information (first optical information) acquired with four types (405 nm, 575 nm, 660 nm and 800 nm) of lights emitted from the lamp unit 250 (see FIG. 22).

Figure 29:
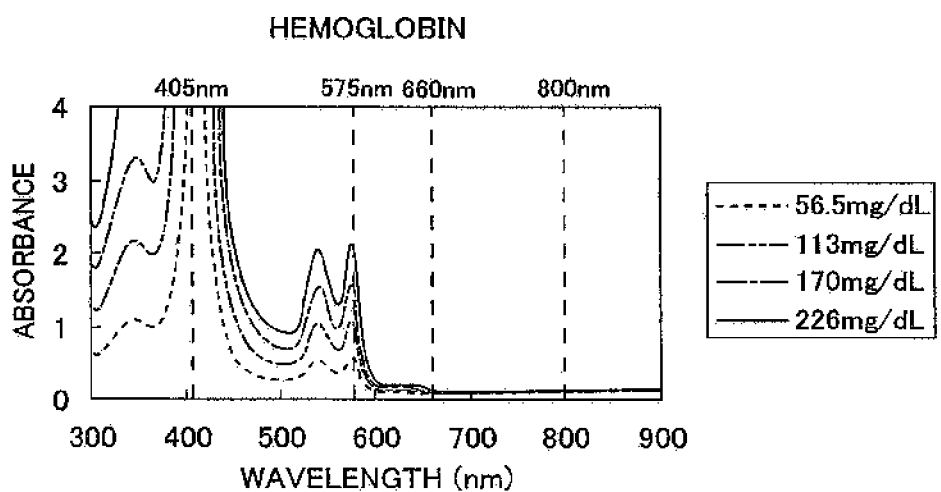
FIG. 29 is a graph showing absorbance spectra of an interference substance (hemoglobin).
Figure 30:
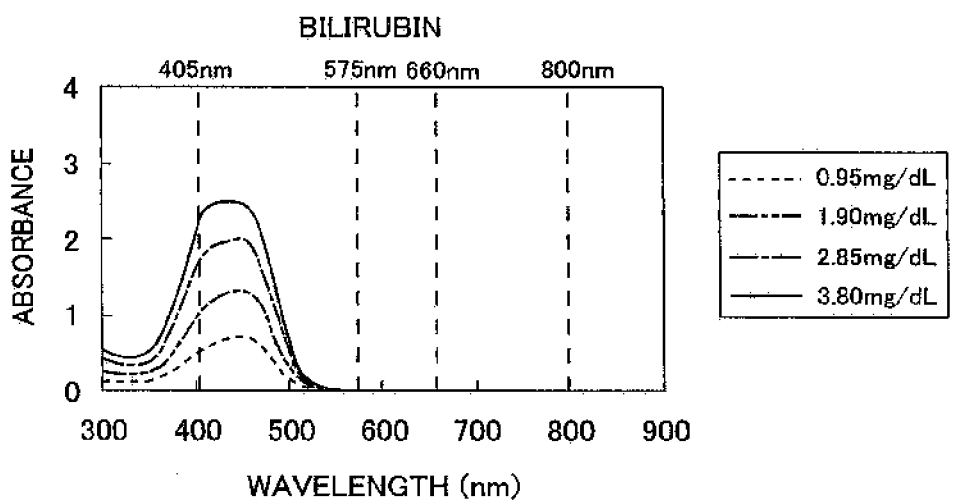
FIG. 30 is a graph showing absorbance spectra of another interference substance (bilirubin).
Figure 31:
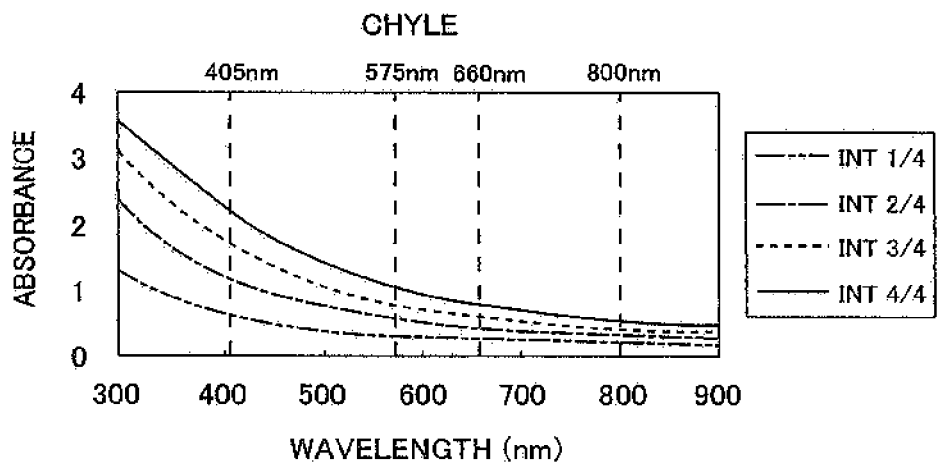
FIG. 31 is a graph showing absorbance spectra of still another interference substance (chyle).

On the basis of the calculated presence/absence and concentrations of interference substances in the specimen, the interference substances are qualitatively determined. As this qualitative determination, there are negativity "−" indicating that the specimen contains substantially no interference substances, weak positivity "+" indicating that the specimen contains prescribed quantities of interference substances and strong positivity "++" indicating that the specimen contains large quantities of interference substances. The results of such qualitative determination are displayed on the display portion 4b of the control unit 4 along with the analysis results obtained at the aforementioned step S111 or the step S112. According to the second embodiment, as hereinabove described, the control portion 4a of the control unit 4 has the structure of comparing the absorbances at the main wavelength and the sub wavelength calculated from the first optical information measured in the first optical information acquisition portion 240 with the thresholds thereby selecting the wavelength employed for analysis and determining whether or not to stop the main measurement, while the present invention is not restricted to this but the control portion 4a may alternatively select the wavelength employed for analysis and determine whether or not to stop the main measurement with the results of qualitative determination on the interference substances obtained in the aforementioned manner. The light having the wavelength of 405 nm is a light absorbed by any of chyle, hemoglobin and bilirubin, as shown in FIGS. 29 to 31. In other words, influences by chyle, hemoglobin and bilirubin contribute to the optical information measured with the light having the wavelength of 405 nm. Further, the light having the wavelength of 575 nm is a light substantially not absorbed by bilirubin but absorbed by chyle and hemoglobin. In other words, influences by chyle and hemoglobin contribute to the optical information measured with the light having the wavelength of 575 nm. In addition, the lights having the wavelengths of 660 nm and 800 nm are lights substantially not absorbed by bilirubin and hemoglobin but absorbed by chyle. In other words, an influence by chyle contributes to the optical information measured with the lights having the wavelengths of 660 nm and 800 nm. As shown in FIG. 31, chyle absorbs the lights of the wavelengths from 405 nm in a low wave range up to 800 nm in a high wave range, and the light having the wavelength of 660 nm is more absorbed by chyle as compared with the light having the wavelength of 800 nm. In other words, the optical information measured with the light having the wavelength of 800 nm is less influenced by chyle than the optical information measured with the light having the wavelength of 660 nm. Wavelengths exhibiting large absorption vary with such interference substances (chyle, hemoglobin and bilirubin), whereby it is possible to select the wavelength employed for analysis and to determine whether or not to stop the main measurement in response to the types of the interference substances contained in the specimen as a result of the qualitative determination. Alternatively, whether or not there are influences by the interference substances may be qualitatively determined every measurement wavelength, without performing the qualitative determination every interference substance. In this case, a wavelength determined as being substantially not influenced by the interference substances may be used for analysis, so that wavelengths determined as being influenced by the interference substances are not employed for analysis.

According to the second embodiment, as hereinabove described, the lamp unit 250 supplying the lights applied to each specimen in the first optical information acquisition portion 240 and the lights applied to each measurement sample in the second optical information acquisition portion 270 is so provided that the lights can be supplied to both of the specimen in the first optical information acquisition portion 240 and the measurement sample in the second optical information acquisition portion 270 with the single lamp unit 250. Thus, the lamp unit 250 for supplying the lights to the specimen in the first optical information acquisition portion 240 and the measurement sample in the second optical information acquisition portion 270 can be employed in common, whereby the specimen analyzing apparatus 201 can be inhibited from size increase.

According to the second embodiment, the lamp unit 250 supplying the lights applied to each specimen in the first optical information acquisition portion 240 and the lights applied to each measurement sample in the second optical information acquisition portion 270 is so provided that substantially homogeneous lights can be supplied to the specimen in the first optical information acquisition portion 240 and the measurement sample in the second optical information acquisition portion 270. Thus, the second optical information acquired from the measurement sample in the second optical information acquisition portion 270 can be correctly estimated from the first optical information acquired from the specimen in the first optical information acquisition portion 240. When the second optical information of the object of analysis is selected from a plurality of second optical information on the basis of the first optical information acquired from the specimen, therefore, any analyzable specimen can be inhibited from being displaced from the object of analysis. Consequently, the number of analyzable specimens can be increased.

According to the second embodiment, the lamp unit 250 is provided with the halogen lamp 251, the single branched optical fiber 258 guiding the lights emitted from the halogen lamp 251 to the specimen in the first optical information acquisition portion 240 and the 11 branched optical fibers 257 guiding the lights emitted from the halogen lamp 251 to the measurement sample in the second optical information acquisition portion 270, whereby substantially homogeneous lights emitted from the halogen lamp 251 can be easily induced to both of the first optical information acquisition portion 240 and the second optical information acquisition portion 270.

According to the second embodiment, the filter portion 253 including the five optical filters 253b to 253f having different light transmission characteristics (transmission wavelengths) is so provided that lights having a plurality of wavelengths can be supplied to the first optical information acquisition portion 240 and the second optical information acquisition portion 270 respectively. Thus, a plurality of first optical information can be acquired by applying the lights having the plurality of wavelengths to the specimen in the first optical information acquisition portion 240, and a plurality of second optical information can be acquired by applying the lights having the plurality of wavelengths to the specimen in the second optical information acquisition portion 270. Consequently, the measurement sample can be measured at a proper wavelength also when the wavelength suitable for measurement of the measurement sample varies with the types of the reagents added to the specimen and the measurement items (PT (prothrombin time), APTT (activated partial thromboplastin time) and Fbg (fibrinogen quantity)).

If the measurement item of the specimen analyzed in the specimen analyzing apparatus 201 according to the second embodiment is "PT", second optical information of the measurement sample acquired with the light having the wavelength (sub wavelength) of 800 nm is analyzed at the step S112 when the absorbance of the specimen acquired with the light having the wavelength of 660 nm (main wavelength) is greater than the threshold (2.0, for example) and the absorbance of the specimen acquired with the light having the wavelength (sub wavelength) of 800 nm is less than the threshold (2.0, for example), whereby the second optical information acquired with the wavelength of 800 nm substantially not influenced by the interference substances (hemoglobin and bilirubin) can be analyzed. Consequently, occurrence of an analytic error resulting from interference substances present in the specimen in analysis of the second optical information can be suppressed.

According to the second embodiment, measurement is stopped at the step S111 when the absorbance of the specimen acquired with the light having the wavelength of 660 nm (main wavelength) is greater than the threshold (2.0, for example) and the absorbance of the specimen acquired with the light having the wavelength (sub wavelength) of 800 nm is greater than the threshold (2.0, for example) so that no reagents are added to a specimen from which reliable results cannot be obtained, whereby the reagents can be inhibited from wasting. Further, no second optical information is acquired from a specimen from which reliable results cannot be obtained, whereby analytical efficiency can also be improved.

The embodiments disclosed this time must be considered as illustrative and not restrictive in all points. The range of the present invention is shown not by the above description of the embodiments but by the scope of claim for patent, and all modifications within the meaning and range equivalent to the scope of claim for patent are included.

Figure 32:
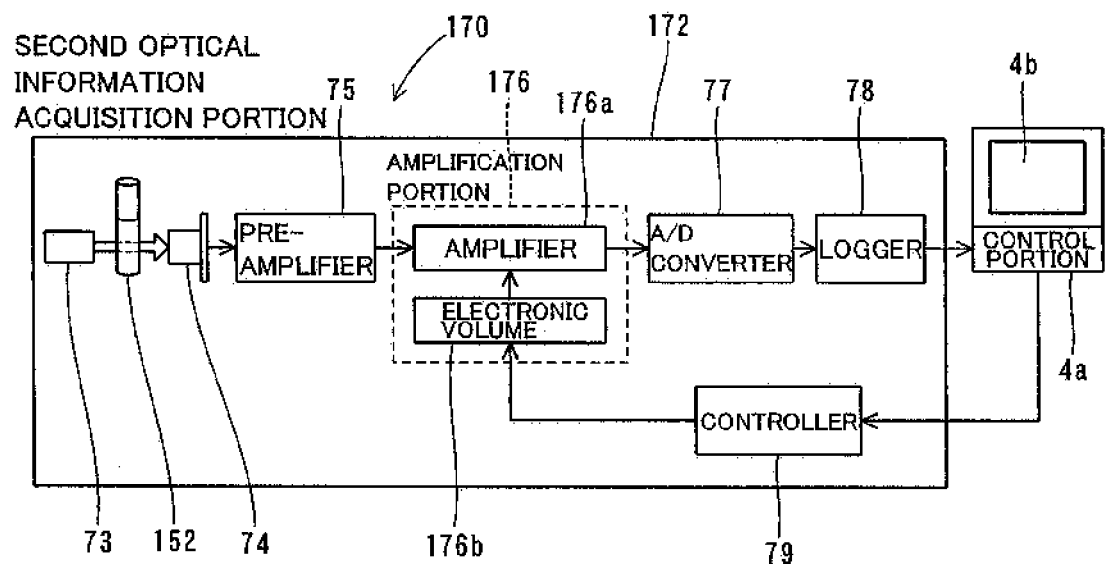
FIG. 32 is a schematic diagram showing the structure of a second optical information acquisition portion according to a modification of the first embodiment of the present invention.

For example, while the example of forming the amplification portion 76 of the detection portion 72 of the second optical information acquisition portion 70 by the amplifier (L) 76a having the prescribed gain (amplification factor), the amplifier (H) 76b having the higher gain (amplification factor) than the amplifier (L) 76a and the changeover switch 76c selecting whether to output the electric signals received from the amplifier (L) 76a to the A/D converter 77 or to output the electric signals received from the amplifier (H) 76b to the A/D converter 77 as shown in FIG. 8 has been shown in the aforementioned first embodiment, the present invention is not restricted to this but an amplification portion 176 of a detection portion 172 of a second optical information acquisition portion 170 may be formed by an amplifier 176a and an electronic volume 176b, as in a modification shown in FIG. 32. In this case, the amplifier 176a of the amplification portion 176 is so formed that the gain (amplification factor) of the amplifier 176a can be adjusted by inputting a control signal from a controller 79 in the electronic volume 176b. When the controller 79 controls the electronic volume 176b in coincidence with the timing of rotation of a filter member 73c in a lamp portion 73 in such a structure, electric signals corresponding to respective lights having different wavelengths emitted from the lamp portion 73 can be amplified with a plurality of different gains (amplification factors).

Figure 33:
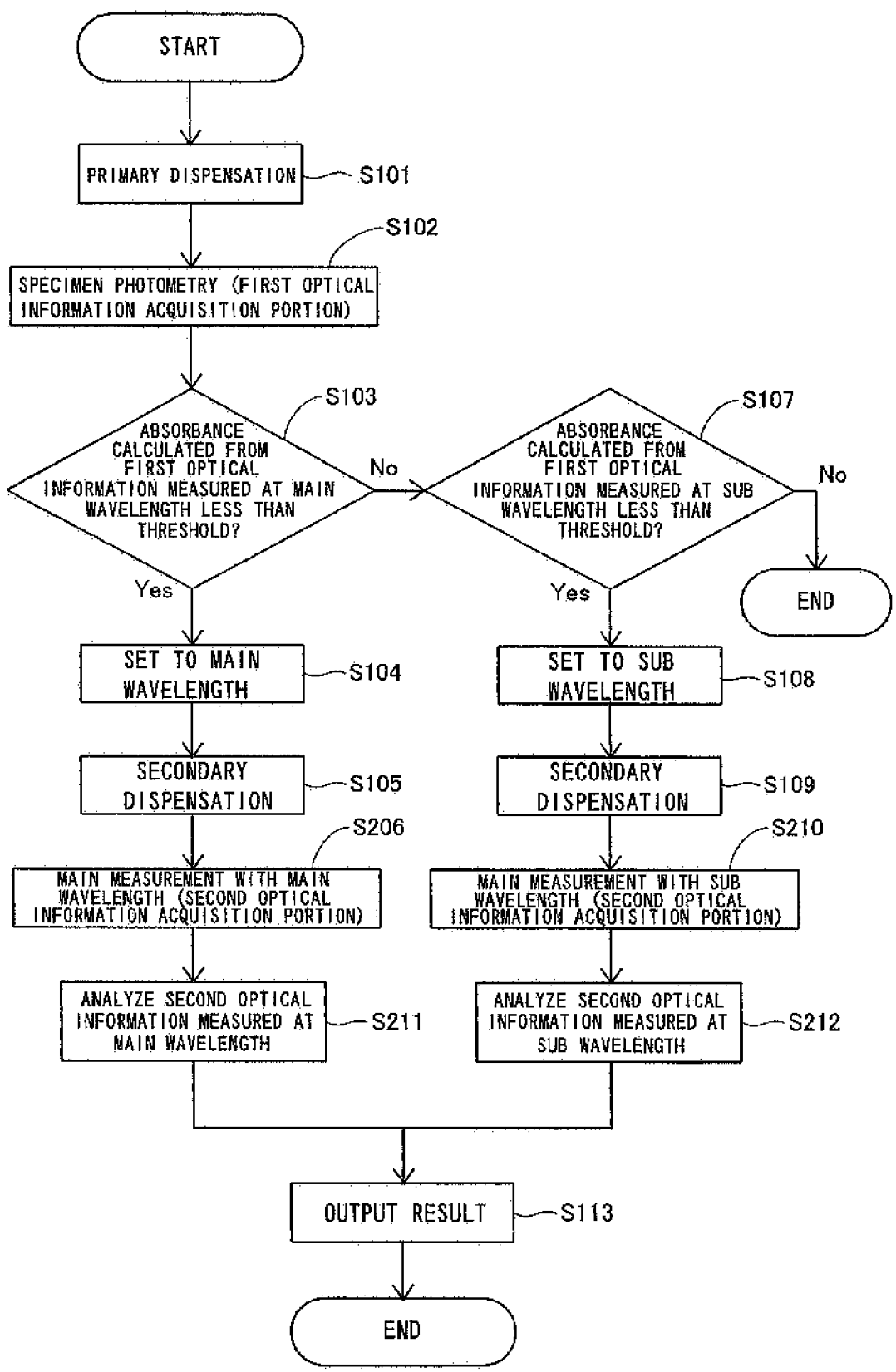
FIG. 33 is a flow chart showing the procedure of a specimen analyzing operation of a specimen analyzing apparatus according to a modification of the second embodiment of the present invention.

While the example of acquiring all of the 10 types of optical information (data of digital signals) from the second optical information acquisition portion including the lamp portion emitting the five lights of different wavelengths and the amplification portion amplifying the electric signals with the two different amplification factors while selecting the second optical information determined as suitable for analysis from among the acquired 10 types of second optical information and analyzing the same on the basis of the analysis results of the first optical information received from the first optical information acquisition portion has been shown in the aforementioned first embodiment, the present invention is not restricted to this but the filter portion 253 in the second embodiment may be rendered stoppable at an arbitrary angle thereby selecting one of the main wavelength, the sub wavelength and stopping of the main measurement as the measurement condition (acquisition condition) and acquiring the second optical information under the selected condition. FIG. 33 is a flow chart showing the procedure of a specimen analyzing operation of a specimen analyzing apparatus according to a modification of the second embodiment. In the flow chart shown in FIG. 33, processing other than steps S206, S210, S211 and S212 is similar to the processing of the second embodiment shown in FIG. 28. If an absorbance at a main wavelength calculated from first optical information measured in a first optical information acquisition portion 240 is less than a threshold at a step S103, a CPU 401a sets an analytic wavelength for acquiring second optical information to a main wavelength at a step S104. At a step S105, secondary dispensation processing is performed, and a measurement sample is prepared. A cuvette 152 of a secondary dispensation table 23 storing the measurement sample is moved into an insertion hole 271a of a cuvette receiving portion 271 of a second optical information acquisition portion 270. At the step S206, a detection portion 272 of the second optical information acquisition portion 270 performs optical measurement (main measurement) on the measurement sample stored in the cuvette 152 under a prescribed condition, thereby acquiring prescribed optical information (second optical information) from the measurement sample. More specifically, rotation of a filter portion 253 is stopped so that a branched optical fiber 257 applies a light of the main wavelength set as the analytic wavelength. The light of the main wavelength applied from the branched optical fiber 257 and transmitted through the cuvette 152 and the measurement sample stored in the cuvette 152 is detected by a photoelectric conversion element 272b. An electric signal corresponding to the light of the main wavelength converted by the photoelectric conversion element 272b is amplified by a preamplifier 272c, and thereafter input in an amplification portion 76.

In the amplification portion 76, the electric signal corresponding to the light of the main wavelength received from the preamplifier 272c (see FIG. 27) is input in an amplifier (H) 76b having a high amplification factor and an amplifier (L) 76a having a normal amplification factor respectively. A controller 79 controls a changeover switch 76c, so that the electric signal amplified by a selected one of the amplifier (H) 76b and the amplifier (L) 76a is output to an A/D converter 77. Thus, a single type of electric signal acquired under a condition suitable for analysis is output to the A/D converter 77. This electric signal is converted to a digital signal by the A/D converter 77, temporarily stored in a logger 78, and thereafter successively transmitted to a control portion 4a of a control unit 4. Thus, acquisition of optical information (second optical information) obtained by measuring the measurement sample at the main wavelength by the second optical information acquisition portion 270 is completed.

If an absorbance at a sub wavelength calculated from first optical information measured in the first optical information acquisition portion 240 is less than a threshold at a step S107, on the other hand, the CPU 401a sets an analytic wavelength for acquiring second optical information to a sub wavelength at a step S108. At steps S109 and S210, rotation of the filter portion 253 is stopped so that a light of the sub wavelength set as the analytic wavelength is applied from the branched optical fiber 257, and the second optical information acquisition portion 270 acquires optical information (second optical information) obtained by measuring the measurement sample at the sub wavelength.

After the acquisition of the second optical information (main measurement) with the second optical information acquisition portion 270 at the aforementioned step S206, a plurality of second optical information measured in the second optical information acquisition portion 270 are transmitted to and analyzed by the control portion 4a of the control portion 4 at the step S211. Thereafter the control portion 4a receiving second optical information acquired at the main wavelength outputs analysis results on the basis of the second optical information.

Similarly, after the acquisition of the second optical information (main measurement) with the second optical information acquisition portion 270 at the aforementioned step S210, a plurality of second optical information measured in the second optical information acquisition portion 270 are transmitted to and analyzed by the control portion 4a of the control unit 4 at the step S212. Thereafter the control portion 4a receiving second optical information acquired at the sub wavelength outputs analysis results on the basis of the second optical information.

Thus, the control portion of the control unit can obtain second optical information suitable for analysis in response to the types of interference substances (hemoglobin, bilirubin and lipid) in the specimen and the degrees of inclusion thereof.

While influences by the interference substances in the main measurement are determined by comparing the absorbances calculated from the first optical information with the thresholds at the steps S103 and S107 in the second embodiment and the aforementioned modification, the present invention is not restricted to this but influences by the interference substances in the main measurement may alternatively be determined by comparing the first optical information with the threshold, for example.

In the aforementioned case of selecting the condition for acquiring second optical information in response to the analytic results of the first optical information acquired by the first optical information acquisition portion, the amplification portion of the second optical information acquisition portion may be constituted of an amplifier (L) 76a having a prescribed gain (amplification factor), an amplifier (H) 76b having a higher gain (amplification factor) than the amplifier (L) 76a and a changeover switch 76c selecting whether to output electric signals received from the amplifier (L) 76a to an A/D converter 77 or to output electric signals received from the amplifier (H) 76b to the A/D converter 77, similarly to the aforementioned first embodiment shown in FIG. 8. According to this structure, either the amplifier (L) 76a or the amplifier (H) 76b can be selected when acquiring second optical information in response to the analysis results of the first optical information obtained by the first optical information acquisition portion 40. Thus, second optical information can be acquired with an amplification factor suitable for analysis by the control portion 4a of the control unit 4 in response to the types of the interference substances in the specimen and the degrees of inclusion thereof.

In the aforementioned case of selecting the condition for acquiring second optical information in response to the analysis results of the first optical information acquired by the first optical information acquisition portion, the amplification portion of the second optical information acquisition portion may be constituted of an amplifier 176a and an electronic volume 176b, similarly to the modification of the aforementioned first embodiment shown in FIG. 32. In this case, the amplifier 176a of an amplification portion 176 is so formed that the gain (amplification factor) of the amplifier 176a can be adjusted by inputting a control signal received from a controller 79 in the electronic volume 176b. Also according to this structure, the gain (amplification factor) of the amplifier 176a can be adjusted to a gain suitable for analysis when second optical information is acquired in response to the analysis results of the first optical information obtained by the first optical information acquisition portion 40.

While the example of applying the lights of three different wavelengths to the specimens stored in the cuvettes with the light-emitting diode (LED) in the first optical information acquisition portion has been described in the aforementioned first embodiment, the present invention is not restricted to this but lights of different wavelengths may alternatively be applied to the specimens stored in the cuvettes from the lamp portion of the second optical information acquisition portion with an optical fiber or the like.

While the example of performing optical measurement (main measurement) of the specimens (measurement samples) with the coagulation time method has been shown in the aforementioned second embodiment, the present invention is not restricted to this but optical measurement of the specimens (measurement samples) may alternatively be performed with the synthetic substrate method or immunonephelometry other than the coagulation time method.

While the examples of providing the detection mechanism portions and the control units independently of each other have been shown in the aforementioned first and second embodiments, the present invention is not restricted to this but the function of the control unit may alternatively be provided on the detection mechanism portion.

What is claimed is:

1. A specimen analyzing method comprising:
    acquiring first optical information by applying a light of a first wavelength, a light of a second wavelength which is longer than the first wavelength, and a light of a third wavelength which is longer than the second wavelength to a first cuvette storing a specimen;
    acquiring information of an interference substance in the specimen based on the first optical information;
    acquiring second optical information by applying at least one of a light of a fourth wavelength, a light of a fifth wavelength which is longer than the fourth wavelength, and a light of a sixth wavelength which is longer than the fifth wavelength to a second cuvette storing a measurement sample prepared from the specimen and a reagent; and
    analyzing the measurement sample based on the second optical information,
    wherein the light of the first wavelength is a light absorbed by a chyle, a hemoglobin and a bilirubin,
    the light of the second wavelength is a light absorbed by the chyle and the hemoglobin, and
    the light of the third wavelength is a light absorbed by the chyle.

2. The specimen analyzing method according to claim 1, further comprising dispensing the specimen into the first cuvette by a specimen pipette.

3. The specimen analyzing method according to claim 2, wherein the specimen is dispensed from a specimen container into the first cuvette.

4. The specimen analyzing method according to claim 1, wherein dispensing the specimen into the second cuvette by a specimen pipette.

5. The specimen analyzing method according to claim 1, wherein the information of the interference substance in the specimen comprises presence or absence of the interference substance in the specimen.

6. The specimen analyzing method according to claim 1, wherein the information of the interference substance in the specimen comprises concentrations of the interference substance in the specimen.

7. The specimen analyzing method according to claim 1, wherein the information of the interference substance in the specimen comprises a result of a qualitative determination on the interference substance in the specimen.

8. The specimen analyzing method according to claim 1, wherein the first wavelength is the fourth wavelength,
    the second wavelength is the fifth wavelength, and
    the third wavelength is the sixth wavelength.

9. The specimen analyzing method according to claim 8, wherein the first wavelength is a wavelength of 405 nm.

10. The specimen analyzing method according to claim 1, wherein the light of the first wavelength is applied by a light source,
    the light of the second wavelength by the light source,
    the light of the third wavelength by the light source,
    the light of the fourth wavelength by the light source,
    the light of the fifth wavelength by the light source, and
    the light of the sixth wavelength by the light source.

11. The specimen analyzing method according to claim 1, further comprising outputting information indicating a measurement item adopted for the specimen and the information of the interference substance corresponding to the measurement item on a display.

12. The specimen analyzing method according to claim 11, wherein the information of the interference substance indicates that there is a high possibility that the specimen is influenced by the chyle.

13. The specimen analyzing method according to claim 11, wherein the information of the interference substance indicates that there is a high possibility that the specimen is influenced by the hemoglobin.

14. The specimen analyzing method according to claim 11, wherein the information of the interference substance indicates that there is a high possibility that the specimen is influenced by the bilirubin.

15. The specimen analyzing method according to claim 1, wherein the measurement item is prothrombin time, activated partial thromboplastin time, antithrombin III, or fibrin decomposition product.

16. A specimen analyzing apparatus comprising:
    a cuvette supplier configured to supply first and second cuvettes configured for optical interrogation;
    a specimen pipette configured to dispense a specimen into first and second cuvettes;
    a reagent holder configured to hold a reagent container;
    a reagent pipette configured to dispense a reagent into the second cuvette so as to prepare a measurement sample;
    an optical information acquiring section configured to acquire first optical information by applying a light of a first wavelength, a light of a second wavelength which is longer than the first wavelength, and a light of a third wavelength which is longer than the second wavelength to the first cuvette and configured to acquire second optical information by applying at least one of a light of a fourth wavelength, a light of a fifth wavelength which is longer than the fourth wavelength, and a light of a sixth wavelength which is longer than the fifth wavelength to the second cuvette;
    a display; and
    a controller programmed to acquire information of the interference substance in the specimen based on the first optical information, and to analyze the measurement sample based on the second optical information,
    wherein the light of the first wavelength is a light absorbed by a chyle, a hemoglobin and a bilirubin,
    the light of the second wavelength is a light absorbed by the chyle and the hemoglobin,
    the light of the third wavelength is a light absorbed by the chyle, and the controller is further programmed to output information indicating a measurement item adopted for the specimen and the information of the interference substance corresponding to the measurement item on the display.

17. The specimen analyzing apparatus according to claim 16, wherein the controller is further programmed to output information indicating a measurement item adopted for the specimen and the information of the interference substance corresponding to the measurement item on the display.

18. The specimen analyzing apparatus according to claim 16, wherein the controller is further programmed to output information indicating that there is a high possibility that the specimen is influenced by the chyle as the information of the interference substance corresponding to the measurement item on the display.

19. The specimen analyzing apparatus according to claim 16, wherein the controller is further programmed to output information indicating that there is a high possibility that the specimen is influenced by the hemoglobin as the information of the interference substance corresponding to the measurement item on the display.

20. A specimen analyzing apparatus comprising:
a cuvette supplier configured to supply first and second cuvettes configured for optical interrogation;
a specimen pipette configured to dispense a specimen into first and second cuvettes;
a reagent holder configured to hold a reagent container;
a reagent pipette configured to dispense a reagent into the second cuvette so as to prepare a measurement sample;
an optical information acquiring section configured to acquire first optical information by applying a light of a first wavelength, a light of a second wavelength which is longer than the first wavelength, and a light of a third wavelength which is longer than the second wavelength to the first cuvette and configured to acquire second optical information by applying at least one of a light of the first wavelength, a light of the second wavelength, and a light of the third wavelength to the second cuvette; and
a controller programmed to acquire information of the interference substance in the specimen based on the first optical information, and to analyze the measurement sample based on the second optical information,
wherein the light of the first wavelength is a light absorbed by a chyle, a hemoglobin and a bilirubin,
the light of the second wavelength is a light absorbed by the chyle and the hemoglobin, and
the light of the third wavelength is a light absorbed by the chyle.

* * * * *